United States Patent
Bhagat

(10) Patent No.: US 10,292,958 B2
(45) Date of Patent: May 21, 2019

(54) LIPID-CONTAINING COMPOSITIONS AND METHODS OF USE THEREOF

(75) Inventor: Urvashi Bhagat, Palo Alto, CA (US)

(73) Assignee: ASHA NUTRITION SCIENCES, INC., Palo Alto, CA (US)

( * ) Notice: Subject to any disclaimer, the term of this patent is extended or adjusted under 35 U.S.C. 154(b) by 0 days.

(21) Appl. No.: 13/332,251

(22) Filed: Dec. 20, 2011

(65) Prior Publication Data

US 2012/0100223 A1  Apr. 26, 2012

Related U.S. Application Data

(62) Division of application No. 12/426,034, filed on Apr. 17, 2009.

(60) Provisional application No. 61/046,747, filed on Apr. 21, 2008, provisional application No. 61/075,708, (Continued)

(51) Int. Cl.

| | | |
|---|---|---|
| A61K 35/20 | (2006.01) |
| A61K 31/535 | (2006.01) |
| A61K 45/00 | (2006.01) |
| A61K 31/353 | (2006.01) |
| A61K 31/575 | (2006.01) |
| A61K 31/405 | (2006.01) |
| A61K 31/7028 | (2006.01) |
| A61K 31/519 | (2006.01) |
| A61K 31/59 | (2006.01) |
| A61K 33/34 | (2006.01) |
| A61K 33/30 | (2006.01) |
| A61K 33/32 | (2006.01) |
| A61K 33/26 | (2006.01) |
| A61K 33/04 | (2006.01) |
| A61K 33/06 | (2006.01) |
| A61K 36/48 | (2006.01) |
| A61K 36/736 | (2006.01) |
| A61K 36/55 | (2006.01) |
| A61K 36/42 | (2006.01) |
| A61K 36/28 | (2006.01) |
| A61K 36/20 | (2006.01) |
| A61K 36/889 | (2006.01) |
| A61K 36/31 | (2006.01) |
| A61K 36/752 | (2006.01) |
| A61K 36/87 | (2006.01) |
| A61K 31/20 | (2006.01) |
| A61K 31/201 | (2006.01) |
| A61K 31/202 | (2006.01) |
| A61P 39/00 | (2006.01) |
| A61P 39/06 | (2006.01) |
| A23D 9/00 | (2006.01) |
| A61K 31/355 | (2006.01) |
| A61K 36/22 | (2006.01) |
| A61K 36/286 | (2006.01) |
| A61K 36/52 | (2006.01) |
| A61K 36/54 | (2006.01) |
| A61K 36/63 | (2006.01) |
| A23L 33/105 | (2016.01) |
| A23L 33/115 | (2016.01) |
| A23L 33/12 | (2016.01) |

(Continued)

(52) U.S. Cl.
CPC ............... *A61K 31/20* (2013.01); *A23D 9/00* (2013.01); *A23L 25/00* (2016.08); *A23L 33/105* (2016.08); *A23L 33/115* (2016.08); *A23L 33/12* (2016.08); *A61K 31/201* (2013.01); *A61K 31/202* (2013.01); *A61K 31/355* (2013.01); *A61K 36/22* (2013.01); *A61K 36/28* (2013.01); *A61K 36/286* (2013.01); *A61K 36/42* (2013.01); *A61K 36/48* (2013.01); *A61K 36/52* (2013.01); *A61K 36/54* (2013.01); *A61K 36/63* (2013.01); *A61K 36/736* (2013.01); *A61K 36/889* (2013.01); *G06F 19/00* (2013.01); *A23V 2002/00* (2013.01); *Y02A 90/26* (2018.01)

(58) Field of Classification Search
None
See application file for complete search history.

(56) References Cited

U.S. PATENT DOCUMENTS

| | | | |
|---|---|---|---|
| 4,784,849 A | 11/1988 | Tutsky | |
| 5,464,643 A | 11/1995 | Lodge | |
| 5,549,905 A * | 8/1996 | Mark et al. | .............. 424/439 |

(Continued)

FOREIGN PATENT DOCUMENTS

| | | |
|---|---|---|
| AU | 2009239499 | 2/2013 |
| AU | 2009239499 | 3/2013 |

(Continued)

OTHER PUBLICATIONS

"Cretan Mediterranean diet for prevention of coronary heart disease" by Renaud et al., Am. J. Clin. Nutr. 1360S-67S (1995).*

(Continued)

*Primary Examiner* — Dennis Heyer
(74) *Attorney, Agent, or Firm* — Cermak Nakajima & McGowan LLP; Malcolm K. McGowan

(57) ABSTRACT

Lipid compositions comprising nuts, seeds, oils, legumes, fruits, grains, and dairy useful in specified amounts as dietary supplements and diet plans designed around and including the aforementioned for the prophylaxis and treatment of numerous diseases are disclosed. The compositions include omega-6 and omega-3 fatty acids where the ratio of the omega-6 to the omega-3 fatty acids and their amounts are controlled based on one or more factors including age of the subject, sex of the subject, diet of the subject, the body weight of the subject, medical conditions of the subject, and climate of the subject's living area.

67 Claims, No Drawings

Related U.S. Application Data filed on Jun. 25, 2008, provisional application No. 61/111,593, filed on Nov. 5, 2008.

(51) Int. Cl.
*A23L 25/00* (2016.01)
*G06F 19/00* (2018.01)

(56) References Cited

U.S. PATENT DOCUMENTS

| | | | |
|---|---|---|---|
| 5,766,621 A | 6/1998 | Trimbo et al. | |
| 5,780,451 A | 7/1998 | DeMichele et al. | |
| 5,962,062 A | 10/1999 | Carrie et al. | |
| 6,036,984 A | 3/2000 | Sartorio et al. | |
| 6,156,369 A | 12/2000 | Eger et al. | |
| 7,759,507 B2 | 7/2010 | Mustad et al. | |
| 2003/0207971 A1 | 11/2003 | Stuart et al. | |
| 2005/0043527 A1* | 2/2005 | Yadav et al. | 536/23.7 |
| 2005/0100621 A1 | 5/2005 | Popp et al. | |
| 2005/0054724 A1 | 10/2005 | Mustad et al. | |
| 2006/0088574 A1 | 4/2006 | Manning et al. | |
| 2006/0127504 A1 | 6/2006 | Peskin | |
| 2007/0010480 A1 | 1/2007 | Rusig et al. | |
| 2008/0019860 A1 | 1/2008 | Abou-Nemeh et al. | |
| 2008/0145506 A1 | 6/2008 | Kane et al. | |

FOREIGN PATENT DOCUMENTS

| | | |
|---|---|---|
| DE | 19948652 A1 | 5/2001 |
| DE | 102004034640 A1 | 2/2006 |
| EP | 0678247 A1 | 10/1995 |
| EP | 0756827 A2 | 2/1997 |
| EP | 1313378 B1 | 5/2003 |
| EP | 1510133 A1 | 3/2005 |
| JP | 03-053869 | 7/1991 |
| RU | 2158514 C1 | 3/2000 |
| RU | 2277354 C2 | 8/2000 |
| RU | 2305416 C2 | 11/2006 |
| WO | 9402166 | 2/1994 |
| WO | 0137678 A1 | 5/2001 |
| WO | 0191575 A1 | 12/2001 |
| WO | 2005065468 | 7/2005 |
| WO | 2006002976 A2 | 1/2006 |
| WO | 2006065735 A1 | 6/2006 |
| WO | 2007080149 A2 | 7/2007 |

OTHER PUBLICATIONS

"Essential Fatty Acids, DHA and Human Brain" by Singh, Indian J. Pediatr. 72, 239-42 (2005).*
"Olives" in web.archive.org/web/20060314112112/http://www.whfoods.com/ genpage.php?pfriendly=1&tname=foodspice&dbid=46 (published: Mar. 14, 2006) (retrieved from the internet Feb. 28, 2016).*
"Olives Nutrient Analysis" in web.archive.org/web/20060344112106/http://www.whfoods.com/genpage.php?tname=nutrientprofile&dbid=111 (published: Mar. 14, 2006) (retrieved from the internet Feb. 28, 2016).*
"Walnuts" in https://web.archive.org/web/20061109221131/http://www.whfoods.com/genpage.php?pfriendly=1&tname=foodspice&dbid=99 (published: Nov. 9, 2006) (retrieved from the internet Feb. 28, 2016).*
"Walnuts Nutrient Analysis" in web.archive.org/web/20061109221127/http://www.whfoods.com/genpage.php? tname=nutrientprofile&dbid=132 (published: Nov. 9, 2006) (retrieved from the internet Feb. 28, 2016).*
Based on Definition in http://legal-dictionary.thefreedictionary.com/based+on (retrieved from the internet Feb. 28, 2016).*
Base Something on Definition in http://www.macmillandictionary.com/us/dictionary/american/base-on (retrieved from the Internet Feb. 28, 2016).*
The Nomenclature of Lipids, J Lipid Res. Jan. 1978;19(1):114-28.*
Olive oil (published: Jul. 14, 2007) at http://web.archive.org/web/20070713174214/http://www.whfoods.com/genpage.php?pfriendly=1&tname=foodspice&dbid=132 (retrieved from the internet Dec. 19, 2016).*
Olive Oil Nutritional Profile (published: Jul. 14, 2007) at http://web.archive.org/web/20070714054939/http://www.whfoods.com/genpage.php?pfriendly=1&tname=nutrientprofile&dbid=110 (Retrieved from the internet Dec. 19, 2016).*
Hammond et al., Soybean Oil; Bailey's Industrial Oil and Fat Products, Sixth Edition, 2005.
ALC, American Lecithin Company, Downloaded from Internet on Dec. 28, 2014.
Scholfield CR, Journal of the American Oil Chemists' Society, vol. 58, No. 10 (Oct. 1981), p. 889-892.
Chaiyasit et al., "Role of Physical Structures in Bulk Oils on Lipid Oxidation," Critical Reviews in Food Science and Nutrition, 47:299-317 (2007).
Chen et al., "Minor Components in Food Oils: A Critical Review of their Roles on Lipid Oxidation Chemistry in Bulk Oils and Emulsions," Critical Reviews in Food Science and Nutrition, 51:901-916 (2011).
Lands WEM, Dietary Fat and Health: the Evidence and the Politics of Prevention, Careful Use of Dietary Fats Can Improve Life and Prevent Disease, Ann. N.Y. Acad. Sci. 1055: 179-192 (2005).
Simopoulos et al., Essentiality of and Recommended Dietary Intakes for Omega-6 and Omega-3 Fatty Acids, Ann Nutr Metab 1999;43:127-130.
Renaud et al., Cretan Mediterranean diet for prevention of coronary heart disease. 1995; 1360S-7S, 61(suppl).
Bhagat et al., "Potential role of dietary lipids in the prophylaxis of some clinical conditions" Arch Med Sci 2015; 11, 4: 807-818.
Duffus JH, "Risk Assessment Terminology" Chemistry International, Mar. 2001, vol. 23, No. 2.
Plenish.com, "A soybean with an enhanced, healthier oil profile" downloaded from the Internet on Aug. 11, 2015.
ASHA Nutrition Sciences, Patents for Humanity USPTO, Humanitarian Use Application, Nov. 8, 2015.
Andreasson, "Emerging roles of PGE2 receptors in models of neurological disease", Prostaglandins & other Lipid Mediators 91 (2010) 104-112.
Baum et al., "Fatty acids in cardiovascular health and disease: A comprehensive update", Journal of Clinical Lipidology (2012) 6, 216-234.
Berglund, "Flax: New Uses and Demands" Trends in new crops and new uses. 2002. J. Janick and A. Whipkey (eds.). ASHS Press, Alexandria, VA.
Brasky et al., "Plasma Phospholipid Fatty Acids and Prostate Cancer Risk in the Select Trial", J Natl Cancer Inst, Jul. 10, 2013.
Calder, "Polyunsaturated fatty acids and inflammatory processes: New twists in an old tale" Biochimie 91 (2009) 791-795.
Chu et al., "A study on vegetable oil blends", Food Chemistry, vol. 62, No. 2, pp. 191-195, 1998.
Fahy et al., "A comprehensive classification system for lipids", J. Lipid Res. 2005. 46: 839-861.
Filho et al., "Essential fatty acids for premenstrual syndrome and their effect on prolactin and total cholesterol levels: a randomized, double blind, placebo-controlled study" Reproductive Health 2011, 8:2.
Fritsche, "Too much linoleic acid promotes inflammation—doesn't it?" Prostaglandins, Leukotrienes and Essential Fatty Acids 79 (2008) 173-175.
Hamazaki et al., "The Japan Society for Lipid Nutrition Recommends to Reduce the Intake of Linoleic Acid" World Rev Nutr Diet. Basel, Karger, 2003, vol. 92, pp. 109-132.
Holman, "The Slow Discovery of the Importance of w3 Essential Fatty Acids in Human Health" J. Nutr. 128: 427S-433S, 1998.
Hulbert et al., "Dietary fats and membrane function: implications for metabolism and disease" Biol. Rev. (2005), 80, pp. 155-169.
Food and Nutrition Board, Institute of Medicine, National Academies, "Dietary Reference Intakes (DRIs)" 2004.

(56) References Cited

OTHER PUBLICATIONS

IUPAC-IUB Commission on Biochemical Nomenclature, "The Nomenclature of Lipids", Physiologische Chemie. vol. 358. pp. 617-631. Jun. 1977.

Ministry of Education, Science and Technology, Japan, "Standard Tables of Food Composition in Japan" Fifth Revised and Enlarged Edition 2005.

Johnson, "Effect of Dietary Linoleic Acid on Markers of Inflammation in Healthy Persons: A Systematic Review of Randomized Controlled Trials", J Acad Nutr Diet. 2012;112:1029-1041.

Lands, "Renewed Questions about Polyunsaturated Fatty Acids" Nutrition Reviews, vol. 44. No. 6, Jun. 1986.

Lu et al., "Linoleic acid suppresses colorectal cancer cell growth by inducing oxidant stress and mitochondrial dysfunction" Lu et al. Lipids in Health and Disease 2010, 9:106.

Morse, "A meta-analysis of blood fatty acids in people with learning disorders with particular interest in arachidonic acid", Prostaglandins, Leukotrienes and Essential Fatty Acids 81(2009)373-389.

O'Leary et al., "Effect of flavonoids and Vitamin E on cyclooxygenase-2 (COX-2) transcription", Mutation Research 551 (2004) 245-254.

Shah et al., "Inhibitory Effect of Curcumin, a Food Spice from Turmeric, on Platelet-Activating Factor- and Arachidonic Acid-Mediated Platelet Aggregation through Inhibition of Thromboxane Formation and Ca2+ Signaling" Biochemical Pharmacology, vol. 58, pp. 1167-1172, 1999.

Silver, "Arachidonic Acid Causes Sudden Death in Rabbits" Science, vol. 183, p. 1085-1086, Mar. 1974.

Simopoulos, "The importance of the ratio of omega-6/omega-3 essential fatty acids", Biomed Pharmacother 56 (2002) 365-379.

Thiebaut et al., "Dietary intakes of x-6 and x-3 polyunsaturated fatty acids and the risk of breast cancer", Int. J. Cancer: 124, 924-931 (2009).

Wu et al., "Age-associated increase in PGE2 synthesis and COX activity in murine macrophages is reversed by vitamin E", Am J Physiol Cell Physiol 275:661-668, 1998.

Yip et al., "The Omega-3 Fatty Acid Eicosapentaenoic Acid Accelerates Disease Progression in a Model of Amyotrophic Lateral Sclerosis", Plos One Apr. 2013 | vol. 8 | Issue 4 | e61626.

* cited by examiner

LIPID-CONTAINING COMPOSITIONS AND METHODS OF USE THEREOF

CROSS-REFERENCE TO RELATED APPLICATION

This application is a divisional of U.S. patent application Ser. No. 12/426,034, filed Apr. 17, 2009, which claims priority to U.S. Patent Application Ser. No. 61/046,747 filed on Apr. 21, 2008, U.S. Patent Application Ser. No. 61/075,708 filed on Jun. 25, 2008, and U.S. Patent Application Ser. No. 61/111,593 filed on Nov. 5, 2008, all of which are incorporated by reference herein in their entireties for all purposes.

BACKGROUND

Fatty acids play important physiological functions. They are the building blocks of phospholipids and glycolipids, crucial components of cell membranes. Fatty acids are the best biological fuel molecules, capable of yielding more than twice as much energy per gram as produced by carbohydrate or protein. Fatty acids directly affect the functions of many proteins through covalent modifications of such proteins. Fatty acids also affect membrane fluidity and associated cellular processes. Fatty acids are also involved in gene regulation, as such may be used to optimize expression of certain genes. Fatty acids' derivatives are also important hormones and biological messengers, e.g., prostaglandins, thromboxanes, leukotrienes, lipoxins, and resolvins. These hormones and messengers affect a broad range of physiological functions such as vasal dilation, platelets aggregation, pain modulation, inflammation, and cell growth.

The human and animal bodies synthesize many kinds of fatty acids of various length of the carbon chain, with various numbers and locations of double bonds. The addition of double bonds into a fatty acid chain converts it into an unsaturated fatty acid, which play significant roles in physiological functions. One way of tracking the location of the double bond in an unsaturated fatty acid molecule is by its distance from the distal carbon, i.e., the omega-carbon. For example, the 18-carbon oleic acid, which has a double bond at the $9^{th}$ carbon from the omega position, is called omega-9 fatty acid. Table 1 below describes various unsaturated fatty acid groups named according to their double bond locations relative to the omega position:

TABLE 1

General Descriptions of Some Fatty Acids

| Name of Fatty Acid | General Formula | Starting Molecule for Biosynthesis |
| --- | --- | --- |
| Omega-3 | $CH_3—CH_2—CH=CH—R—COOH$ | Alpha-Linolemic Acid |
| Omega-6 | $CH_3—(CH_2)_4—CH=CH—R—COOH$ | Linoleic Acid |
| Omega-7 | $CH_3—(CH_2)_5—CH=CH—R—COOH$ | Palmitoleic Acid |
| Omega-9 | $CH_3—(CH_2)_7—CH=CH—R—COOH$ | Oleic Acid |

As shown in the table above, Linoleic acid (LA) and Alpha-linolenic Acid (ALA) are the precursors for all omega-6 and omega-3 fatty acids. It is well established that LA and ALA are "essential" fatty acids. They must be supplied in the diet because the human and other mammalians cannot synthesize them from other sources. Dietary deficiency or excess of the two essential fatty acids may cause many illnesses. It is also well known that LA and ALA share the same metabolic pathways, and that the excess of one can increase the need for, or create a deficiency of, the other. Along with LA and ALA, certain other fatty acids, such as Oleic acid and certain saturated fatty acids are also considered important for human nutrition even though the body can make them. The latest science also shows evidence that non-essential fatty acids though beneficial in optimal quantities, can interfere with the activity and metabolism of essential fatty acids when in excess, and that the quantity of dietary fat can also influence the metabolism of fatty acids. ALA is known to be preferentially metabolized by the human body depending on the amount of the other fatty acids present in the diet.

Evidence also shows that antioxidants, phytochemicals, microorganisms, vitamins and minerals, other dietary factors including proteins and carbohydrates, and hormones and genes also play a role in metabolism of essential fatty acids. Furthermore, human studies have identified that males and females appear to differ in their ability to metabolize essential fatty acids. It has been suggested that sex hormones play a role in these differences. Molecules of polyunsaturated fatty acids have a zigzag-like structure because of the double bonds. Because they are flexible and do not pack tightly, they stay fluid even at cold temperatures and collectively lend flexibility to tissues. Hence, in colder climates the human body benefits from greater amounts of polyunsaturated fatty acids. However, the greater the number of double bonds in a lipid molecule, the greater the susceptibility to per-oxidation, which may be associated with a number of diseases and may accelerate aging. This is another reason for cautious consumption of polyunsaturated fatty acids.

Numerous studies provide evidence for the prophylaxis and treatment of medical conditions using supplementation with omega-3 fatty acids and recommendations to reduce omega-6 fatty acid consumption. The medical conditions implicated include menopause, cardiovascular diseases, mental disorders, neural disorders, musculoskeletal disorders, endocrine disorders, cancer, digestive system disorders, symptoms of aging, viral infections, bacterial infections, obesity, overweight, renal diseases, pulmonary disorders, ophthalmologic disorders, dermatological disorders, sleep disorders, dental diseases, and the diseases of the immune system including autoimmunity. For example, U.S. Pat. No. 5,780,451 taught lipid formulations for patients with ulcerative colitis, which include omega-3, omega-6, and omega-9 fatty acids. The omega-3 fatty acid content in these lipid formulations was significantly high. Similarly, a recently published U.S. patent application, US2008/0039525, disclosed lipid compositions used for diabetic patients, which contained omega-3, omega-6, and omega-9 fatty acids, with the specific ratio of omega-6 to omega-3 being between 0.25:1 to 3:1.

The traditional emphasis on increasing omega-3 fatty acids and reducing omega-6 fatty acids consumption often does not result in satisfactory relieves because of the uncertainties introduced by dietary and demographic factors. Accordingly, improved methods and treatments, using improved lipid compositions, for the medical conditions and for prophylaxis are still needed. In fact, on Jan. 26, 2009, for the first time the American Heart Association issued an advisory to correct the perception that omega-6 fatty acids are unhealthy. Harris et al., Omega-6 Fatty Acids and Risk and Cardiovascular Disease. A Science Advisory From the American Heart Association Nutrition Subcommittee of the Council on Nutrition, Physical Activity, and Metabolism; Council on Cardiovascular Nursing; and Council on Epidemiology and Prevention. Circulation. 2009;119;902-907. The current methodologies are contusing for the consumer, hence lead to over consumption or under consumption of critical nutrients with major health consequences.

BRIEF SUMMARY

The present disclosure relates to compositions and methods for prophylaxis and/or treatment of medical conditions linked with an imbalance in one or more lipids within context of other factors. More particularly, the present disclosure relates to the use of compositions and methods that use more advantageous sources of omega-6 fatty acids, in the presence of nutritionally adequate omega-3 fatty acids. The disclosure also relates to methods and compositions that deliver omega-6 and omega-3 fatty acids along with other nutrients that optimize the daily delivery and bioavailability of omega-6 and omega-3 for prophylaxis and/or treatment of medical conditions linked with an imbalance in one or more lipids. This disclosure also relates to methods of steady delivery of the bioactive substances, daily, weekly, monthly or longer duration wide and sudden fluctuations of which may be harmful. Furthermore, this disclosure also relates to methods of daily delivery of essential fatty acids within the optimal range with respect to the recommendations.

One general embodiment of the present disclosure is a lipid-containing composition comprising optimal amounts of fatty acids, antioxidants, minerals, and phytochemicals/plant matter for a mammalian subject based on one or more factors selected from the group including the subject's age, sex, diet, bodyweight, physical activity, medical conditions, and the climate of the subject's living area. Such composition is administered to a subject through a steady delivery process, as explained later, according to one embodiment of the disclosure. According to another embodiment of the disclosure, the fatty acid, antioxidant, mineral, and phytochemical components of the composition's lipid contents are achieved at least in part by using one or more of the following concentrated lipid sources: oils, butters, nuts, and seeds.

Another embodiment of the disclosure is a lipid-containing composition comprising polyunsaturated, monounsaturated, and saturated fatty acids, wherein the ratios and amounts of said three fatty acid types are controlled based on one or more of the following factors for a mammalian subject: age, sex, climate, body weight, physical activity, diet, and medical conditions.

Another aspect of the present disclosure is a specific lipid composition suitable for administration to a mammalian subject. One embodiment of such composition comprises three or more of the following substances (or the oil thereof) in certain defined concentrations: peanuts, almonds, olives, soybeans, cashews, flaxseeds, pistachios, pumpkin seeds, sunflower seeds, sesame seeds, walnuts, anhydrous butter oil, and coconut meat. Another example of such composition comprises three or more of a safflower oil, sunflower oil, peanut oil, almond oil, corn oil, and anhydrous butter oil.

Another aspect of the present disclosure is directed at methods of prophylaxis or treatment of a medical condition for a mammalian subject, said method comprising administering a therapeutically effective amount of balanced lipid formula to said subject, preferably replacing the unbalanced fats typically added to foods in the form of oils, butters, nuts and seeds and the like.

Yet another aspect of the present disclosure is directed at methods of creating lipid and other nutrients-balanced diet by combining special formulated lipid composition with lipid-free food.

DETAILED DESCRIPTION

As used herein, "prophylaxis" refers to the preservation of health, a preventive treatment, or a treatment meant to reduce the risk of a medical condition.

As used herein, the term "treatment" in the context of a medical condition refers to the management of the condition and may or may not involve the complete amelioration of the condition.

As used herein, "medical condition" is a disease, disorder, syndrome, and the like; or a symptom thereof.

As used herein a "lipid imbalance" refers to a suboptimal/undesirable lipid profile in blood or other tissue of a mammal, or a deficiency or excess of one or more lipids as compared with a medical norm or as indicated by the manifestation of a disorder. It is understood that the body's defense mechanisms (such as storage of essential fatty acids among others) can help compensate for a deficiency or excess of a particular fatty acid to a limited extent.

As used herein a "therapeutically effective amount" is an amount of a composition that results in the prophylaxis and/or treatment of a medical condition or symptom of a medical condition. In some embodiments, the adverse level of a biomarker or the severity of a symptom of the medical condition is abated at least 10% or more, at least 25% or more, at least 50% or more, at least 75% or more, or 100% ameliorated.

As used herein the phrase "adequate amount of omega-3 fatty acids" refers to a minimum of dietary reference intake (DRI) levels of omega-3 fatty acids per day from foods, supplements, and/or the lipid compositions.

A "therapeutic effect," as that term is used herein, encompasses a therapeutic benefit and/or a prophylactic benefit. By therapeutic benefit is meant eradication or amelioration of the underlying disorder being treated. Also, a therapeutic benefit may be achieved with the eradication or amelioration of one or more of the physiological symptoms associated with the underlying disorder such that an improvement may be observed in the patient, notwithstanding that the patient may still be afflicted with the underlying disorder. For prophylactic benefit, the compositions may be administered to a patient/individual at risk of developing a particular disease, or to a patient/person reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

The present disclosure, in one embodiment, provides a lipid-containing composition comprising daily optimal amounts of fatty acids and phytochemicals for a mammalian subject based on one or more factors selected from the following group: age of the subject, sex of the subject, diet of the subject, the body weight of the subject, medical conditions of the subject, and climate of the subject's living area. In one aspect, the composition is administered to the subject by steady delivery.

In another embodiment, such composition further comprises omega-6 and omega-3 fatty acids and wherein the ratio of omega-6 to omega-3 fatty acids and their amounts are controlled based on one or more factors selected from said group. In one aspect, said ratio of omega-6 to omega-3 fatty acid is in the range of 4:1 to 45:1. In another aspect, said ratio of omega-6 to omega-3 fatty acid is in the range of 1:1 to 10:1 and said subject has a diet of low anti-oxidants and/or low phytochemicals. In yet another aspect, the composition further comprises one or more omega-9 fatty acids wherein the ratio of omega-9 to omega-6 fatty acids is also determined based on one or more factors selected from said group.

In one aspect of the above composition, said ratio of omega-9 to omega-6 is in the range of 1:1 to 5:1; said ratio of omega-6 to omega-3 is in the range of 1:1 to 45:1; and said medical condition is associated with a form of lipid imbalance.

In another aspect of the above composition, said omega-9 fatty acid is in the range of 10% to 80% of total lipids in the composition; said omega-6 fatty acid is in the range of 4% to 60% of total lipids in the composition; and said omega-3 fatty acid is in the range of 0.3% to 20% of total lipids in the composition.

In any of the above embodiments, the fatty acid components of the composition is achieved at least in part by using one or more of the following concentrated lipid sources: oils, butters, nuts, and seeds. In any of the above embodiment, the group further includes lipid tolerance of said subject.

In another embodiment, the composition of the any of the above embodiments is used as a dietary component.

In yet another embodiment, in the composition, said omega-9 is in the range of 15% to 80% of total lipids in the composition and wherein said omega-6 is in the range of 8% to 60% of total lipids in the composition and omega-3 in the range of 0.3% to 12% of total lipids in the composition. In one aspect, the composition further comprises: a vitamin E wherein an amount of the vitamin E is in the range of 0.001% to 0.2% of total lipids in the composition.

The subject can be an omnivorous human, or a human with low antioxidant and/or low phytochemical diet, said omega-9 lipids being in the range of 15% to 80% of total lipids in the composition, wherein said omega-6 are in the range of 6% to 53% of total lipids in the composition and said omega-3 lipids are in the range of 1% to 18% of total lipids in the composition. In one aspect, the composition further comprises: a vitamin E in the range of 0.005% to 0.2% of total lipids in the composition.

Also provided in the present disclosure, in one embodiment, is a lipid-containing composition comprising polyunsaturated, monounsaturated, and saturated fatty acids, wherein the ratios and amounts of said three fatty acid types are controlled based on one or more of the following factors for a mammalian subject: age, sex, climate, body weight, diet, and medical conditions. In some aspects, additional nutrients are also controlled based on one or more of said factors and wherein said additional nutrients are one or more components selected from the following group: phytochemicals, antioxidants, vitamins, and minerals.

Another embodiment of the present disclosure provides a method of creating a balanced diet plans, using a composition of any of the above embodiment. In one aspect, lipid-free or low-lipid foods are designed for use in combination with said lipid composition to achieve a balanced diet plan.

In one aspect, the ratio of a total fatty acid content to monounsaturated content in the composition is in the range of 1.25:1 to 4:1; the ratio of monounsaturated to polyunsaturated fatty acids in the composition is in the range of 1:1 to 3:1; and the ratio of monounsaturated fatty acids to saturated fatty acids in the composition is in the range of 1:1 to 5:1.

In another aspect, the composition comprises one or more of the following components: peanut oil, vegetable oil, avocado oil, olive oil, sunflower oil, safflower oil. In yet another aspect, the composition further comprises one or more of the following components: mustard oil, palm oil, and soybean lecithin.

One embodiment of the composition comprises three or more of the following components:
 a peanut oil present at 8 to 56 percent by weight in said composition;
 a vegetable oil present at 8 to 46 percent by weight in said composition;
 an avocado oil present at 3 to 16 percent by weight in said composition;
 an olive oil present at 5 to 32 percent by weight in said composition;
 a sunflower oil present at 6 to 34 percent by weight in said composition; and
 a safflower oil present at 2 to 30 percent by weight in said composition.

In one embodiment, said controlled fatty acid components come from one or more of the following nuts and seeds: peanuts, almonds, olives, soybeans, cashews, pistachios, pumpkin seeds, sunflower seeds, walnuts, coconut meat. In one aspect, said controlled fatty acid components further come from anhydrous butter.

Yet another embodiment of the present disclosure provides a lipid-containing composition suitable for administration to a mammalian subject, the lipid composition comprising three or more of the following components:
 peanuts present at 2 to 11 percent by weight in said composition;
 almonds present at 5 to 32 percent by weight in said composition;
 olives present at 6 to 36 percent by weight in said composition;
 soybeans present at 4 to 25 percent by weight in said composition;
 cashews present at 4 to 21 percent by weight in said composition;
 pistachios present at 2 to 9 percent by weight in said composition;
 pumpkin seeds present at 2 to 15 percent by weight in said composition;
 sunflower seeds present at 1 to 4 percent by weight in said composition;
 walnuts present at 3 to 25 percent by weight in said composition;
 anhydrous butter present at 4 to 24 percent by weight in said composition; and
 coconut meat present at 1 to 6 percent by weight in said composition.

Also provided is a lipid-containing composition suitable for administration to a mammalian subject, the lipid composition comprising three or more of the following components:
 an almond oil present at 2 to 23 percent by weight in said composition;
 an avocado oil present at 1 to 7 percent by weight in said composition;
 a soybean oil present at 1 to 7 percent by weight in said composition;
 a cashew oil present at 2 to 15 percent by weight in said composition;

a pistachio oil present at 1 to 7 percent by weight in said composition;
a pumpkin seed oil present at 1 to 8 percent by weight in said composition;
a walnut oil present at 3 to 25 percent by weight in said composition;
a peanut oil present at 5 to 30 percent by weight in said composition;
a corn oil present at 3 to 19 percent by weight in said composition;
an olive oil present at 3 to 17 percent by weight in said composition;
a safflower oil present at 1 to 14 percent by weight in said composition; and
an anhydrous butter oil present at 5 to 29 percent by weight in said composition.

Still a further embodiment provides a method of prophylaxis or treatment of a medical condition for a mammalian subject, said method comprising administering a therapeutically effective amount of the composition of any of the above embodiment to said subject, wherein said medical condition is linked with a lipid Imbalance in said mammalian subject. In one aspect, said medical condition is selected from the group consisting of: a symptom of menopause, a cardiovascular disease, a mental disorder, a neural disorder, a musculoskeletal disorder, an endocrine disorder, a cancer, a digestive system disorder, a symptom of aging, a viral infection, a bacterial infection, obesity, overweight, a renal disease, a pulmonary disorder, an ophthalmologic disorder, a dermatological disorder, a sleep disorder, a dental disease, an immune system disease, and an autoimmunity.

Further provided, in one embodiment, is a lipid composition suitable for administration to a mammalian subject, the lipid composition comprising three or more of the following components:
an almond oil present at 1 to 36 percent by weight in said composition;
a pumpkin seed oil present at 1 to 24 percent by weight in said composition;
an oil from walnuts present at 2 to 36 percent by weight in said composition;
a peanut oil present at 4 to 72 percent by weight in said composition;
a corn oil present at 1 to 24 percent by weight in said composition;
an olive oil present at 2 to 36 percent by weight in said composition;
a sunflower oil present at 4 to 72 percent by weight in said composition;
a safflower oil present at 2 to 60 percent by weight in said composition; and
an anhydrous butter oil present at 2 to 36 percent by weight in said composition.

In one aspect, the composition further comprises one or more of the following: a mustard oil present at 8 percent or less by weight in said composition, a flaxseed oil present at 8 percent or less by weight in said composition, a palm oil present at 2 percent or less by weight in said composition, a coconut oil present at 8 percent or less by weight in said composition, and a soybean lecithin present at 4 percent or less by weight in said composition.

One embodiment of the present disclosure provides a lipid-containing composition suitable for administration to a mammalian subject wherein the lipid components are controlled based on the seasonal climate of the subject's Irving area.

In one aspect, said seasonal climate has a daytime high temperature range and said composition has corresponding lipid components selected from the temperature range group in Table 6 said lipid components comprise three or more components selected from the components in the table.

In another aspect, the composition further comprises one or more additional components selected from one of the additional component in Table 6 corresponding to the daytime high temperatures.

Yet another embodiment of the present disclosure provides a lipid-containing composition suitable for administration to a mammalian subject, wherein the subject is in an environment with a given or forecasted ambient daily high temperature, and wherein the lipid-containing composition and a temperature range of the given or forecasted ambient daily high temperature are selected from the group consisting of:
the lipid-containing composition includes one or more omega-9 lipid present in a range of 20 to 90 percent by weight of total lipid, the lipid-containing composition includes one or more omega-6 lipid present in a range of 4 to 60 percent by weight of total lipid, the lipid-containing composition includes one or more omega-3 lipid present in a range of 0.3 to 5 percent by weight of total lipid, and the temperature range is from about 90 to about 135 degrees Fahrenheit;
the lipid-containing composition includes one or more omega-9 lipid present in a range of 20 to 90 percent by weight of total lipid, the lipid-containing composition includes one or more omega-6 lipid present in a range of 4 to 60 percent by weight of total lipid, the lipid-containing composition includes one or more omega-3 lipid present in a range of 0.5 to 6.0 percent by weight of total lipid, and the temperature range is from about 70 to about 99 degrees Fahrenheit;
the lipid-containing composition includes one or more omega-9 lipid present in a range of 20 to 90 percent by weight of total lipid, the lipid-containing composition includes one or more omega-6 lipid present in a range of 6 to 60 percent by weight of total lipid, the lipid-containing composition includes one or more omega-3 lipid present in a range of 0.8 to 7.0 percent by weight of total lipid, and the temperature range is from about 50 to about 75 degrees Fahrenheit;
the lipid-containing composition includes one or more omega-9 lipid present in a range of 10 to 80 percent by weight of total lipid, the lipid-containing composition includes one or more omega-6 lipid present in a range of 10 to 60 percent by weight of total lipid, the lipid-containing composition includes one or more omega-3 lipid present in a range of 1 to 8.0 percent by weight of total lipid, and the temperature range is from about 33 to about 55 degrees Fahrenheit;
the lipid-containing composition includes one or more omega-9 lipid present in a range of 10 to 80 percent by weight of total lipid, the lipid-containing composition includes one or more omega-6 lipid present in a range of 12 to 70 percent by weight of total lipid, the lipid-containing composition includes one or more omega-3 lipid present in a range of 1.5 to 0.0 percent by weight of total lipid, and the temperature range is from about 0 to about 37 degrees Fahrenheit;
the lipid-containing composition includes one or more omega-9 lipid present in a range of 10 to 80 percent by weight of total lipid, the lipid-containing composition includes one or more omega-6 lipid present in a range of 13 to 70 percent by weight of total lipid, the lipid-containing composition includes one or more omega-3 lipid present in a range of 1.8 to 12.0 percent by weight of total lipid, and the temperature range is from about −50 to about 5 degrees Fahrenheit; and the lipid-containing composition includes one or more omega-9 lipid present in a range of 10 to 80 percent by weight of total lipid, the lipid-containing composition includes one or more omega-6 lipid present in a range of 15 to 73 percent by weight of total lipid, the lipid-containing composition includes one or more omega-3 lipid present in a range of 2.0 to 13.0 percent by weight of total lipid, and the temperature range is from about −100 to about −45 degrees Fahrenheit.

In one aspect of the above embodiment, the composition further comprises one or both of the following components: a vitamin E alpha present in a range of 0.005 to 0.2 percent by weight of total lipid; and a vitamin E gamma present in a range of 0.001 to 0.04 percent by weight of total lipid.

Another embodiment of the present disclosure provides a lipid-containing composition suitable for administration to a mammalian subject, comprising: total lipids which consist of one or more monounsaturated lipids, one or more polyunsaturated lipids, and one or more saturated lipids; wherein the subject is in an environment with a given or forecasted ambient daily high temperature; and wherein the lipid-containing composition and a temperature range of the given or forecasted ambient daily high temperature are selected from one of the following groups:

the ratio of the total lipids to the monounsaturated lipids is in a range of 1.0:1.0 to 4.5:1.0, the ratio of the total lipids to the polyunsaturated lipids is 1.7:1.0 to 15.0:1.0, and the ratio of the total lipids to the saturated lipids is 2.0:1.0 to 10.0:1.0, and the temperature range is from about 90 to about 135 degrees Fahrenheit;

the ratio of the total lipids to the monounsaturated lipids is in a range of 1.0:1.0 to 4.5:1.0, the ratio of the total lipids to the polyunsaturated lipids is in a range of 1.5:1.0 to 10.0:1.0, and the ratio of the total lipids to the saturated lipids is in a range of 2.0:1.0 to 10.0:1.0, and the temperature range is from about 70 to about 99 degrees Fahrenheit;

the ratio of the total lipids to the monounsaturated lipids is in a range of 1.0:1.0 to 4.5:1.0, the ratio of the total lipids to the polyunsaturated lipids is in a range of 1.5:1.0 to 8.0:1.0, and the ratio of the total lipids to the saturated lipids is in a range of 2.0:1.0 to 10.0:1.0, and the temperature range is from about 50 to about 75 degrees Fahrenheit;

the ratio of the total lipids to the monounsaturated lipids is in a range of 1.0:1.0 to 4.5:1.0, the ratio of the total lipids to the polyunsaturated lipids is in a range of 1.4:1.0 to 7.0:1.0, and the ratio of the total lipids to the saturated lipids is in a range of 2.0:1.0 to 11.0:1.0, and the temperature range is from about 33 to about 55 degrees Fahrenheit;

the ratio of the total lipids to the monounsaturated lipids is in a range of 1.0:1.0 to 5.0:1.0, the ratio of the total lipids to the polyunsaturated lipids is in a range of 1.3:1.0 to 6.5:1.0, and the ratio of the total lipids to the saturated lipids is in a range of 2.0:1.0 to 11.0:1.0, and the temperature range is from about 0 to about 37 degrees Fahrenheit;

the ratio of the total lipids to the monounsaturated lipids is in a range of 1.0:1.0 to 5.0:1.0, the ratio of the total lipids to the polyunsaturated lipids is in a range of 1.2:1.0 to 6.0:1.0, and the ratio of the total lipids to the saturated lipids is in a range of 2.0:1.0 to 11.0:1.0, and the temperature range is from about −50 to about 5 degrees Fahrenheit; and the ratio of the total lipids to the monounsaturated lipids is in a range of 1.0:1.0 to 5.0:1.0, the ratio of the total lipids to the polyunsaturated lipids is in a range of 1.1:1.0 to 5.0:1.0, and the ratio of the total lipids to the saturated lipids is in a range of 2.0:1.0 to 11.0:1.0, and the temperature range is from about −100 to about −45 degrees Fahrenheit.

In one aspect of the above embodiment, the composition further comprises one or both of the following components: a vitamin E alpha present in a range of 0.005 to 0.2 percent by weight of total lipid; and a vitamin E gamma present in a range of 0.001 to 0.04 percent by weight of total lipid.

Further provided is a composition comprising safflower oil, sunflower oil, almond oil, and anhydrous butter oil. Another embodiment provides a composition comprising olive oil and sunflower oil, wherein the amount of one or more omega-6 lipids in the composition is greater than 20% of total lipids in the composition. Also provided is a composition comprising anhydrous butter oil wherein the ratio of omega-6 lipids to omega-3 lipids in the composition is 8:1 to 12:1.

Lipid Formulations

In one aspect, the present disclosure incorporates relatively high ratio of omega-6 to omega-3 fatty acid, while maintaining optimal daily delivery of both omega-6 and omega-3 fatty acids. One reason for maintaining the high ratio is because of the incorporation of nuts, seeds, and nut oils as integral components of a formulation, which nuts, seeds, and nut oils have high antioxidants, minerals and phytochemical content and other properties that may render excessive omega-3 unnecessary. In some instances, excessive omega-3 (which have 3 to 6 double bonds) may be associated with per-oxidative stress. Certain embodiments of the present disclosure may favor in-vivo formation of Linoleic acid metabolites Gamma-linolenic acid (3 double bonds) and Dihomo-gamma-linolenic acid (3 double bonds), which may have dose-dependent anti-inflammatory properties and other health benefits. Nuts and seeds may have a narrow therapeutic window, unfavorable interactions, and other properties requiring judicious use; therefore the formulations deliver measured and optimized quantities of nuts and seeds along with oils.

Certain embodiments of the present disclosure provide for compositions comprising supplementation with one or more of following: Vitamin A, B9 (folic acid), C, D, E; alkaloids, carotenoids like beta-carotene, lycopene, astaxanthin, lutein, zeaxanthin; monophenols; polyphenols, flavonoids stilbenes, flavonols such as quercetin, kaempferol, and resveratrol, flavanones, flavones, flavan-3-ols such as catechins, anthocyanins and anthocyanodins, isoflavones; phytoestrogens; phytosterols such campesterol, sitosterol, and stigmasterol; phenolic acids such as gallic acid, ellagic acids, and curcumin; hydroxycinnamic acids such as coumarins; organosulfides; saponins, terpenoids, lactones; melatonin; lignans; and antioxidants and phytochemicals in general. In certain embodiments, each of these supplements/nutrients may reduce/alter the requirement for omega-3 fatty acids and allow for a higher omega-6 to omega-3 ratio than in the absence of said supplement(s)/nutrient(s). in certain embodiments, minerals and trace elements such as Na, K, Ca, Mg, Fe, Cu, Zn, Mn, and Se may also alter the metabolism and/or requirements tolerance for omega-6 and omega-3 fatty acids. In certain embodiments each of the above nutrients is optimized through natural sources such as oils, butters, nuts and seeds, herbs, sweeteners, and other foods.

Nuts and seeds are plant embryos containing plant stem cells. They are made to survive the harshest of the climactic conditions until factors are suitable for germination. As such, gram per gram, they are one of the richest sources of natural nutrients. Almonds are one of the most nutritionally dense nuts, providing an array of powerful nutrients: flavonoids, vitamin E, manganese, magnesium, copper, vitamin B2 and phosphorus, to name a few. The flavonoids found in nuts, particularly almond skins, together with the vitamin E found in their meat double the antioxidants that either delivers separately.

Walnuts, pecans and chestnuts have the highest antioxidant content of the tree nuts, with walnuts delivering more than 20 mmol antioxidants per 3 ounces, including at least 16 antioxidant phenols, vitamin E, and ellagic and gallic acid. Walnuts are also exceptionally high in their content of the omega-6 fatty acid linoleic acid and the omega-3 fatty acid alpha-linolenic acid.

Peanuts also contribute significantly to dietary intake of antioxidants, rivaling the antioxidant content of blackberries and strawberries, and are far richer in antioxidants than apples, carrots or beets. Peanuts are a good source of vitamin E (gamma- and alpha-tocopherol), niacin, folate, proteins, and manganese. Peanuts also contain high concentrations of phytochemicals polyphenols, including resveratrol.

Sesame seeds are a very good source of manganese, copper, calcium, magnesium, iron, phosphorus, vitamin B1, zinc and dietary fiber. In addition to these important nutrients, sesame seeds contain lignans, sesamin and sesamolin, and phytosterols. Sesame seeds have the highest total phytosterol content (400-413 mg per 100 grams) of all nuts and seeds; pistachios and sunflower seeds are the second richest (270-289 mg/100 g), closely followed by pumpkin seeds (265 mg/100 g).

A quarter cup of sunflower seeds may provide 31.9% of the daily value for magnesium. Sunflower seeds are also a good source of selenium. Cashews, flaxseeds, pumpkin seeds, and sesame seeds are a good source of magnesium. Almonds, cashews, sunflower seeds, pumpkin seeds, walnuts, and sesame seeds are a good source of copper. Almonds, flaxseeds, peanuts, sunflower seeds, pumpkin seeds, and walnuts are a good source of manganese. Just one-quarter cup of almonds may supply 45.0% of the daily value for manganese, and 20.0% of the daily value for copper.

In one aspect, the disclosure provides compositions that include seeds, nuts, and/or oils. In another aspect the compositions include legumes, dairy, cocoa, lentils, and/or grains. In one embodiment the composition can include one or more edible oils, culinary nuts and/or seeds in their whole form or their oils such as, but not limited to acai oil, amaranth oil, apple seed oil, apricot kernel oil, argan oil, artichoke oil, avocado oil, babassu oil, ben oil, blackcurrant seed oil, borage seed oil, borneo tallow nut oil, bottle gourd oil, buffalo gourd oil, butter oil (anhydrous), canola oil (rapeseed), cape chestnut oil, carob pod oil, cocklebur oil, cocoa butter oil, cohune oil, coriander seed oil, corn oil, cottonseed oil, dika oil, evening primrose oil, false flax oil (camelina sativa), fish oil (cod liver), fish oil (herring), fish oil (menhaden), fish oil (salmon), fish oil (sardine), grapeseed oil, household lard, kapok seed oil, lallemantia oil, marula oil, meadowfoam seed oil, mustard oil, nutmeg butter, okra seed oil, palm oil, papaya seed oil, pequi oil, perilla oil, prune kernel oil, quinoa oil, ramtil oil, rice bran oil, royle oil, sacha inchi oil, safflower oil, sheanut oil, soybean lecithin oil, tea oil, thistle oil, tomato seed oil, ucuhuba butter oil, wheat germ oil, acorns, almonds, beech nuts, brazilnuts, breadnuts, candlenuts, chestnuts, chilacayote nuts, chilean hazel nuts, coconuts, cashews, colocynth nuts, filberts, hazelnut, hickory, kola nut, macadamia, mamoncillo, melon seeds, mongongo, obongo nut, olives, peanuts, pecans, pili nuts, pine nuts, pistachios, soya nuts, poppy seeds, pumpkin seeds, hemp seeds, flax seeds, sesame seeds, sunflower seeds, walnuts, and watermelon seeds.

In some embodiments, the compositions of the present disclosure include the following optimally balanced fatty acids and combinations thereof. Saturated fatty acids: butyric (C4:0), lauric (C12:0), myristic (C14:0), palmitic (C16:0), stearic (C18:0), and arachidic (C20:0); monounsaturated fatty acids: myristoleic (C14:1), palmitoleic (C16:1), and omega-9 oleic (C18:1), gadoleic (C20:1), erucic (C22:1), and nervonic (C24:1); and polyunsaturated fatty acids: omega-6 linoleic (C18:2), conjugated-linoleic (C18:2), gamma-linolenic (C18:3), eicosadienoic (C20:2), di-homo-gamma-linolenic (C20:3), and arachidonic (C20:4); and omega-3 alpha-linolenic (C18:3), stearidonic (C 8:4), eicosapentaenoic (C20:5), docosapentaenoic (C22:5), and docosahexaenoic (C22:6) fatty acids.

In some embodiments, synergy among complementing nutrients from different sources may be incorporated. For example, in-vivo oxidation may take different pathways; use of optimal mix of antioxidants may be more effective in managing different pathways, providing for moderate level of oxidation necessary for physiology. Furthermore, using different sources avoids concentrated delivery of specific antioxidants and phytochemicals that may be harmful in excess (for example, some phytosterols), since nuts and seeds are known to have strong positive and negative outcomes. In one embodiment, Ayurvedic principles (ancient Indian medicine proven empirically over centuries) around the use of oils, nuts, and seeds may be integrated with western molecular science to design various lipid-containing compositions.

Given below in Table 2 are some examples of components of oils. USDA, National Nutrient Database for Standard Reference (available online) can be consulted for detailed components of various oils, nuts and seeds.

TABLE 2

Relevant Components of Dietary Oils

| Nutrient | Units | Peanut Oil 1 tbsp | Corn Oil 1 tbsp | Sunflower Oil (high linoleic) 1 tbsp | Fish Oil (herring) 1 tbsp | Butter Oil (Anhydrous) 1 tbsp | Coconut Oil 1 tbsp |
|---|---|---|---|---|---|---|---|
| Total lipid (fat) | g | 13.5 | 13.6 | 13.6 | 13.6 | 12.73 | 13.6 |
| Total Saturated Fatty Acids | g | 2.281 | 1.761 | 1.401 | 2.895 | 7.926 | 11.764 |
| Total Monounsaturated Fatty Acids | g | 6.237 | 3.75 | 2.652 | 7.693 | 3.678 | 0.789 |
| Total Polyunsaturated Fatty Acids | g | 4.32 | 7.436 | 8.935 | 2.122 | 0.473 | 0.245 |
| Butyric Acid (C4:0) | g | | | | | 0.413 | |

TABLE 2-continued

Relevant Components of Dietary Oils

| Nutrient | Units | Peanut Oil 1 tbsp | Corn Oil 1 tbsp | Sunflower Oil (high linoleic) 1 tbsp | Fish Oil (herring) 1 tbsp | Butter Oil (Anhydrous) 1 tbsp | Coconut Oil 1 tbsp |
|---|---|---|---|---|---|---|---|
| Caproic Acid (C6:0) | g | | | | | 0.244 | 0.082 |
| Caprylic Acid (C8:0) | g | | | | | 0.142 | 1.02 |
| Capric Acid (C10:0) | g | | | | | 0.319 | 0.816 |
| Lauric Acid (C12:0) | g | | | | 0.021 | 0.358 | 6.066 |
| Myristic Acid(C14:0) | g | 0.014 | 0.003 | | 0.977 | 1.281 | 2.285 |
| Palmitic Acid (C16:0) | g | 1.282 | 1.439 | 0.802 | 1.592 | 3.349 | 1.115 |
| Margaric Acid (C17:0) | g | | 0.009 | | | | |
| Stearic Acid (C18:0) | g | 0.297 | 0.251 | 0.612 | 0.111 | 1.543 | 0.381 |
| Arachidic Acid (C20:0) | g | 0.189 | 0.059 | | | | |
| Behenic Acid (C22:0) | g | 0.378 | | | | | |
| Lignoceric Acid (C24:0) | g | 0.121 | | | | | |
| Palmitoleic Acid (C16:1) | g | 0.014 | 0.016 | | 1.311 | 0.285 | |
| Oleic Acid (C18:1, n − 9) | g | 6.048 | 3.717 | 2.652 | 1.626 | 3.203 | 0.789 |
| Gadoleic Acid (C20:1, n − 9) | g | 0.176 | 0.018 | | 1.853 | | |
| Erucic Acid (C22:1, n − 9) | g | | | | 2.803 | | |
| Linoleic Acid (C18:2, n − 6) | g | 4.32 | 7.278 | 8.935 | 0.156 | 0.288 | 0.245 |
| Alpha-linolenic Acid (C18:3, n − 3) | g | | 0.158 | | 0.104 | 0.185 | |
| Arachidonic Acid (C20:4, n − 6) | g | | | | 0.039 | | |
| Eicosapentaenoic Acid (C20:5 n − 3) | g | | | | 0.853 | | |
| Docosapentaenoic Acid (C22:5 n − 3) | g | | | | 0.084 | | |
| Docosahexaenoic Acid (C22:6 n − 3) | g | | | | 0.572 | | |
| Vitamin A, RAE | mcg | | | | | 108 | |
| Retinol | mcg | | | | | 105 | |
| Carotene, beta | mcg | | | | | 25 | |
| Vitamin A, IU | IU | | | | | 393 | |
| Vitamin E (alpha-tocopherol) | mg | 2.12 | 1.94 | 5.59 | | 0.36 | 0.01 |
| Tocopherol, beta | mg | 0.06 | | | | | |
| Tocopherol, gamma | mg | 2.15 | | | | | 0.03 |
| Tocopherol, delta | mg | 0.18 | | | | | |
| Vitamin K (phylloquinone) | mcg | 0.1 | 0.3 | 0.7 | | 1.1 | 0.1 |
| Phytosterols | mg | 28 | 132 | 14 | | | 12 |

In a related aspect, the disclosure provides compositions that include polyunsaturated fatty acids, monounsaturated fatty acids, saturated fatty acids, including omega-3, omega-6, and omega-9 fatty acids. In some embodiments the composition is a liquid formulation. In other embodiments the composition is a solid formulation. In yet other embodiments the composition is a semi-solid formulation. In certain embodiments, the composition can substitute the unbalanced fats (cooking oils, fats, and the like) that are typically added to various food preparations and/or supplement fats contained in an individual's diet from other sources. In certain embodiments, in addition to normal lipid-containing ingredients, the disclosure may further comprise herbs, spices, sweeteners, and additives. In certain embodiments, lipid-free or low-lipid diet plans are developed to complement the composition. In certain embodiments, the entire diet is a composition, balanced with respect to fatty acids, antioxidants, phytochemicals, vitamins, and minerals. In some embodiments, the disclosure includes compositions wherein the ratios and daily delivery of omega-3, omega-6 and omega-9 and other fatty acids are in an amount sufficient to prevent the onset or progression of, protect from the severity of, or decrease a medical condition or disorder, or a symptom there. In particular embodiments, the compositions described herein are formulated with respect to one or more of an individual's factors including but not limited to diet, gender, age, categories such as infants, babies, children, adolescent, and adults, size, weight, medical conditions, family medical history, climate and other demographic factors. In case of infants and babies the compositions may be formulated with respect to the mother's factors. The compositions may be delivered by any acceptable delivery method; in certain embodiments vitamins and minerals may be added to the compositions, and in certain embodiments, an additional vitamin and mineral supplement may be administered.

In one embodiment, an individual with a herbivorous diet, an ovo-lacto vegetarian diet, a vegan diet, or a high-antioxidant high-phytochemical omnivorous diet may be administered related compositions. In another aspect, an individual with a low-antioxidant low-phytochemical herbivorous diet, a low-antioxidant low-phytochemical ovo-lacto vegetarian diet, a low-antioxidant low-phytochemical vegan diet, or a low-antioxidant low-phytochemical omnivorous diet may be administered related compositions. In another aspect, an individual may be administered with compositions that are formulated with respect to whether his or her diet comprises a low or high intake of seafood. This pertains to concentrated lipid compositions. One method of measuring antioxidant and phytochemical consumption is to measure the number of fruits, vegetables, whole grains, and legumes servings per day, where two or more per day may provide high-antioxidant, high-phytochemical content. However, two or more servings of foods such as white rice or potatoes may contain very little phytochemicals. Yet certain other foods, particularly certain herbs such as turmeric may contain potent phytochemicals (even in small quantities, e.g., a quarter-teaspoon). Therefore, the disclosure provides a number of different compositions, including one with varying levels of omega-3 fatty acids to suit a consumer's diet and/or tolerance level. As used herein, "tolerance" and the like mean the ability of a consumer to withstand the composition without any discomfort. In some embodiments, the compositions designed for consumers with high seafood diet (two or more seafood servings per week), include low amount of nuts and seeds. In some instances, no nuts or seeds are included. Other phytochemicals may also be minimized or eliminated as part of a composition to avoid unfavorable interactions. The method is shown schematically in Table 3.

TABLE 3

Schematic representation for developing tailored dietary lipid programs and for optimizing dietary nutrients.

|  | High phytochemicals | High meat | High seafood |
|---|---|---|---|
| 1. Develop dietary cohorts[a,b] | | | |
| Grains | | | |
| Brown Rice | --to-- cups/g | --to-- cups/g | --to-- cups/g |
| Whole Wheat | --to-- cups/g | --to-- cups/g | --to-- cups/g |
| Other | --to-- cups/g | --to-- cups/g | --to-- cups/g |
| Vegetables | Develop ranges as above | | |
| Fruits | Develop ranges as above | | |
| Legumes | Develop ranges as above | | |
| Dairy | Develop ranges as above | | |
| Meats | Develop ranges as above | | |
| Seafood | Develop ranges as above | | |
| Herbs | Develop ranges as above | | |
| Sweeteners | Develop ranges as above | | |
| Beverages | Develop ranges as above | | |
| 2. Compute range of nutrients | | | |
| Lipids | | | |
| C4:0 | --to-- mg | --to-- mg | --to-- mg |
| C22:6 w/3 | --to-- mg | --to-- mg | --to-- mg |
| Other | --to-- mg | --to-- mg | --to-- mg |
| Carbohydrates | Compute ranges as above | | |
| Protein | Compute ranges as above | | |
| Vitamins | Compute ranges as above | | |
| Minerals | Compute ranges as above | | |
| Phytochemicals | Compute ranges as above | | |
| Antioxidants | Compute ranges as above | | |
| 3. Develop lipid programs | | | |

Develop lipid programs to complement the nutrients above, from natural oils, nuts, seeds, and herbs; additional vitamins and minerals may be used. Deliver as diurnal mutually complementing individual dosages: daily variety may strengthen compliance.

| Monday | Oil blend-A + sauce-A + spread-A + dessert-A |
| Tuesday | Oil blend-B + sauce-B + spread-B + dessert-B |
| Other | Oil blend-X + sauce-X + spread-X + dessert-X |

[a]Based on average daily consumption.
[b]Further customizations may address age, gender, climactic temperature, and medical conditions/lipid tolerance.

Administration

In some embodiments, the compositions comprising the lipid formulation disclosed herein may be administered to an individual in any orally accepted form. The lipid formulations may be packaged in one, two, three, four or more mutually complementing daily dosages. In some embodiments, they may be contained in any one or more of, but not limited to, a single dosage or sustained and controlled release capsule, soft-gel capsule, hard capsule, tablet, powder, lozenge, or pill prepared in some instances with carriers such as starches, sugars, diluents, granulating agents, lubricants, binders, disintegrating agents, and the like; a powder such as infant formula or a granule; a body food; nutritional bar; a bakery food product such as a bread, a dessert, a pastry, a truffle, a pudding or cake; a sealed single dosage packet or resealable packaging containing a liquid, an oil blend, a gel, a sauce, a dressing, a spread, a butter, drops, a semi-solid; liquid, or the like; or a cooking oil such as a frying oil, a pan-frying oil, a parting oil or the like. In some embodiments, they may be unsealed and taken orally, or added as part of a cooking ingredient to previously cooked or uncooked food preparation with or without added fat. For example, they can be made into special cooking oil, butter, dressing, etc. and be added into foods while such foods are being prepared. In certain embodiments, some or all of the components of the compositions may be skinned and/or unskinned, pre-soaked and/or un-soaked, sprouted and/or un-spouted, cut and/or uncut, diced, shredded, pureed, grinded, blended, grilled, baked, roasted, sautéed, and/or cooked or uncooked, unprocessed and/or processed by any other method. The components of the compositions may be delivered in one-part or multiple parts as various components of a meal or to complement a meal, for example. In some embodiments, the lipid-containing compositions may be delivered using a gelatinous case, a vial, a pouch or a foil for containing such compositions. In some embodiments, they may be part of an enteral or parenteral formula, or a combination thereof. In some embodiments a one-day, one-week, two-week, bi-weekly, bi-monthly, or monthly diet plan may be formulated comprising various lipid formulations described herein, with varying compositions administered each day.

The balanced lipid composition disclosed herein may be used to create a completely balanced diet plan, by adding the composition, which contains balanced components of lipids, phytochemicals, antioxidants, vitamins, and minerals to name a few, into foods as a dietary component. In one embodiment, a dietary component can be a cooking ingredient added to prepared or unprepared food or beverage. In some embodiments, it can also be a finished food product such as a dessert or side dish, which are served together with other components of a meal. Special foods containing no lipid or low lipids (for example small amounts of lipids contained in meats, poultry, seafood, milk, fruits, vegetables, and grains) may be created to be used together with balanced lipid formulation to ensure the complete balance of the lipid intake. Again, the administration of the balanced composite nutrients may be achieved through one course in a meal or multiple courses in a meal (e.g., salad, main course, and dessert).

Each individual may be given instructions on use of the product, and risk and cautionary measures, as is usual with any pharmaceutical, nutraceutical, or any product intended for ingestion. Oils, nuts, seeds, and herbs are potent; therefore, instructions may include recommended dosage, frequency, and suggestions for optimization. For example, sesame seeds, particularly in large amounts may induce uterine contractions, and therefore pregnant women may be cautioned against the use of certain compositions comprising sesame seeds before full-term; such compositions however may be beneficial for certain other conditions.

The delivery of the desired lipid composition may be achieved through a one-part or multi-part mutually complementing delivery system. For example, the desired formulation may be achieved through adding various components to various parts of a meal, including bread, salad, main course, and/or dessert.

One aspect of the disclosure is to deliver fatty acids in such a way that the total daily delivery of omega-6 and omega-3 from the lipid composition and the rest of the diet are optimal with respect to daily recommendations.

Yet another aspect of the present disclosure is the concept of steady delivery of fatty acids, with respect to phytochemicals, antioxidants, and minerals, based on the observation that each time there is a change in dietary lipid delivery/consumption, it upsets the body physiology, sometimes with adverse effects such as headaches, muscle and joint pains, digestive and bowel upset, mental confusion, and anxiety; and at other times it may cause short-lived euphoria and general sense of wellness. Though the body adapts to the change in 2-3 weeks or longer, long-term effects of the change/consumption outside the optimal range may be harmful. Furthermore, sudden large fluctuations in fatty acids can also have acute adverse effects. Sudden withdrawal of a habitual high long-chain omega-3 fatty acids or immunosuppressive phytochemical/nutrient supply from the host, or sudden increase in omega-6 fatty acids may result in release of a cytokine storm, with severe consequences involving systemic inflammatory response (capillary leakage, pyrexia, tachycardia, tachypnoea), multi-organ dysfunction (gastrointestinal, lungs, liver, kidney, heart), and connective tissue damage in the joints. At such instances the host may be most vulnerable to infections, myocardial infarction, stroke, and induction of psoriasis depending upon the rest of the body chemistry and the presence of infectious agents. In less severe manifestations, due to moderate fluctuations in fatty acids and in otherwise salubrious condition, the host may experience sleep disturbance, headaches, muscle cramps, confusion, melancholia, and rage resulting from changes in neurotransmission, excitability of muscle and neural cells, fluctuating eicosanoids, and androgens. This steady delivery requires a steady dosage within the optimal range lasting approximately 2 to 3 weeks at a minimum.

EXAMPLES

Example 1

Formulas with Various Lipid Ratios

In specific embodiments of the disclosure the formulations described herein have high antioxidant and phytochemical content and properties that render extra omega-3 unnecessary. In specific embodiments sterols and lignans (such as in sesame), sweeteners (such as honey), and herbs/spices (such as turmeric) included in the compositions can render extra omega-3 unnecessary. The formulations may provide a balanced fatty acid composition of approximately 10-100 grams of total daily fat. The formulations may include specific ratios of various lipid components as shown below in Table 3. The ratios may be weight by weight, weight by volume, or volume by volume (w/w, w/v, or v/v).

TABLE 4

Lipid Ratios

| Lipid Component Ratio | Approximate Ratio Range |
|---|---|
| Omega-6 to Omega-3 Fatty Acids | 1:1-50:1 |
| Omega-9 to Omega-6 Fatty Acids | 0.5:1-6:1 |
| Total Fatty Acids to Monounsaturated Fatty Acids | 1:1-15:1 |
| Monounsaturated to Polyunsaturated Fatty Acids | 0.25:1-6:1 |
| Monounsaturated to Saturated Fatty Acids | 0.25:1-7:1 |
| Total Fatty Acids to Polyunsaturated Fatty Acids | 1:1-15:1 |
| Total Fatty Acids to Saturated Fatty Acids | 1:1-15:1 |

In some embodiments, the lipid formulation calls for specific percentages of omega-9, omega-6, and omega-3 fatty acids, as shown in Table 5 below.

TABLE 5

Contents of Various Unsaturated Fatty Acids

| Lipid Name | Content (w/w, w/v, or v/v of total lipids) |
|---|---|
| Omega-9 | 10-90% |
| Omega-6 | 4-75% |
| Omega-3 | 0.1-30% |
| Vitamin E-alpha/gamma | 0.001-0.5% |

Example 2

Lipid Compositions According to Climate

In one embodiment, compositions of the disclosure are formulated as per climatic condition and ambient temperature range. Table 6 provides % by weight ranges for a lipid formulation that includes oils, nuts and seeds as disclosed by embodiments of the present disclosure, by climatic condition and temperature range.

TABLE 6

Lipid Formulation According to Climate

% by Weight Ranges by Temperature (in ° F.)

| | HOT 90°-135° | | WARM 70°-99° | | COOL 50°-75° | | COLD 33°-55° | | BELOW FREEZING 0°-37° | | ARCTIC −50°-5° | | POLAR −100°-−45° | |
|---|---|---|---|---|---|---|---|---|---|---|---|---|---|---|
| | Low | High | Low | High | Low | High | Low | High | Low | High | Low | High | Low | High |
| Oils | | | | | | | | | | | | | | |
| Anhydrous Butter Oil | 2 | 36 | 2 | 30 | 1 | 29 | 2 | 28 | 2 | 30 | 2 | 30 | 2 | 30 |
| Avocado Oil | 0 | 15 | 0 | 15 | | | | | | | | | | |
| Coconut Oil | 0 | 25 | | | | | | | | | | | | |
| Corn Oil | | | 0 | 15 | 0 | 15 | 0 | 15 | 2 | 30 | 2 | 30 | 2 | 30 |
| Cotton seed oil | 0 | 15 | 0 | 15 | 0 | 15 | 0 | 15 | 0 | 15 | 0 | 15 | 0 | 15 |
| Fish Oil | | | 0 | 15 | 0 | 15 | 0 | 15 | 0 | 20 | 0 | 20 | 0 | 20 |
| Grapeseed oil | 0 | 15 | 0 | 15 | 0 | 15 | 0 | 15 | 0 | 15 | 0 | 15 | 0 | 15 |
| Hemp oil | 0 | 15 | 0 | 15 | 0 | 15 | 0 | 15 | 0 | 15 | 0 | 15 | 0 | 15 |
| Mustard Oil | | | | | 0 | 15 | 0 | 35 | 0 | 20 | 0 | 20 | 0 | 20 |
| Olive Oil | | | 1 | 30 | 1 | 29 | 2 | 30 | 2 | 30 | 4 | 60 | 4 | 60 |
| Palm Oil | | | 0 | 5 | 0 | 5 | 0 | 5 | 0 | 5 | 0 | 5 | 0 | 1 |
| Peanut Oil | 2 | 68 | 2 | 53 | 0 | 35 | | | | | | | | |
| Perrilla oil | 0 | 15 | 0 | 15 | 0 | 15 | 0 | 15 | 0 | 15 | 0 | 15 | 0 | 15 |
| Rapeseed Oil | 0 | 15 | 0 | 15 | 0 | 15 | 0 | 30 | 2 | 30 | 0 | 30 | 0 | 30 |
| Rice Bran Oil | 0 | 15 | 0 | 15 | 0 | 15 | 0 | 15 | 0 | 15 | 0 | 15 | 0 | 15 |

TABLE 6-continued

Lipid Formulation According to Climate

% by Weight Ranges by Temperature (in °F.)

| | HOT 90°-135° | | WARM 70°-99° | | COOL 50°-75° | | COLD 33°-55° | | BELOW FREEZING 0°-37° | | ARCTIC −50°-5° | | POLAR −100°-−45° | |
|---|---|---|---|---|---|---|---|---|---|---|---|---|---|---|
| | Low | High | Low | High | Low | High | Low | High | Low | High | Low | High | Low | High |
| Safflower Oil | 2 | 68 | 2 | 53 | 1 | 29 | 2 | 30 | 2 | 30 | 2 | 30 | 2 | 30 |
| Soybean Lecithin | 0 | 2 | 0 | 2 | 0 | 2 | 0 | 2 | 0 | 2 | 0 | 2 | 0 | 1 |
| Sunflower Oil | 4 | 72 | 2 | 53 | 1 | 37 | 2 | 30 | 2 | 30 | 2 | 30 | 2 | 30 |
| Wheatgerm oil | | | | | 0 | 10 | 0 | 10 | 0 | 10 | 0 | 10 | 0 | 10 |
| Nuts and Seeds | | | | | | | | | | | | | | |
| Almonds | 3 | 48 | 3 | 49 | 2 | 47 | 3 | 46 | 3 | 48 | 3 | 48 | 3 | 48 |
| Brazilnut | | | | | 0 | 10 | 0 | 15 | 0 | 5 | 0 | 15 | 0 | 15 |
| Cashews | 2 | 37 | 2 | 31 | 1 | 20 | 1 | 18 | | | | | | |
| Chestnut | | | | | | | 0 | 15 | 0 | 15 | 0 | 15 | 0 | 15 |
| Coconut | 0 | 25 | 0 | 10 | 0 | 10 | 0 | 5 | 0 | 5 | 0 | 5 | 0 | 4 |
| Flaxseed | | | | | 0 | 20 | 0 | 15 | 1 | 10 | 0 | 17 | 0 | 17 |
| Hazelnut | | | | | 0 | 10 | 0 | 15 | 0 | 15 | 0 | 15 | 0 | 15 |
| Macadamia Nuts | | | | | 0 | 10 | 0 | 15 | 0 | 15 | 0 | 15 | 0 | 15 |
| Olives | 2 | 33 | 2 | 28 | 1 | 28 | 2 | 27 | 2 | 28 | 2 | 28 | 2 | 28 |
| Peanuts | | | | | 1 | 33 | 2 | 38 | 3 | 47 | 3 | 47 | 3 | 47 |
| Pine nuts | | | | | | | 0 | 15 | 0 | 15 | 0 | 15 | 0 | 15 |
| Pistachios | | | 1 | 20 | 1 | 17 | 1 | 15 | 1 | 14 | 0 | 14 | 0 | 14 |
| Pumpkin seeds | 3 | 54 | 3 | 46 | 2 | 45 | 3 | 43 | | | | | | |
| Sesame | | | | | 0 | 10 | 0 | 15 | 0 | 15 | 0 | 15 | 0 | 15 |
| Soybeans | | | 2 | 34 | 1 | 34 | 2 | 33 | 2 | 34 | 2 | 34 | 2 | 34 |
| Sunflower Seeds | 1 | 15 | 1 | 15 | 0 | 10 | 1 | 10 | | | | | | |
| Walnuts | 2 | 33 | 2 | 28 | 1 | 27 | 2 | 26 | 2 | 27 | 2 | 27 | 2 | 27 |

Table 7 provides % by weight ranges (% of weight of the entire composition) for omega-9, omega-6, and omega-3 fatty acids as disclosed by embodiments of the present disclosure, by climatic condition and temperature range.

TABLE 7

Unsaturated Fatty Acid Contents According to Climate

% by Weight Ranges by Temperature (in °F.)

| | HOT 90°-135° | | WARM 70°-99° | | COOL 50°-75° | | COLD 33°-55° | | BELOW FREEZING 0°-37° | | ARCTIC −50°-5° | | POLAR −100°-−45° | |
|---|---|---|---|---|---|---|---|---|---|---|---|---|---|---|
| | Low | High | Low | High | Low | High | Low | High | Low | High | Low | High | Low | High |
| Omega-9 Fats | 20 | 90 | 20 | 90 | 20 | 90 | 10 | 80 | 10 | 80 | 10 | 80 | 10 | 80 |
| Omega-6 Fats | 4 | 60 | 4 | 60 | 6 | 60 | 10 | 60 | 12 | 70 | 13 | 70 | 15 | 73 |
| Omega-3 Fats | 0.3 | 5 | 0.5 | 6 | 0.8 | 7 | 1 | 8 | 1.5 | 12 | 1.8 | 15 | 2 | 20 |

In the following example, specific lipid compositions were prepared for healthy individuals living in a variety of climates, with a high antioxidant/phytochemical diet and/or a vegetarian diet, for maintenance of general health and well-being. The compositions were made up of a variety of oils, nuts and seeds, as described in Table 6. The compositions presented in Table 8 were formulated by three different methods: lipid liquid formulation only, a solid or semi-solid nut and seed formulation only, or a combination formulation containing oils, nuts and seeds. The compositions were formulated to be administered in a once a day format (combined formulation), or a twice a day format where one administration was of the liquid lipid formation and the other administration was of the solid nut and seed composition.

Table 8 provides the omega-6 to omega-3 ratio contained in the lipid compositions of this example for a range of climates. The ratios are presented, for any one of the liquid only, solid only, or combination formulations.

TABLE 8

Ratio of Omega-6 (O6) to Omega-3 (O3) by Climate

| | O6:O3 Ratio by Climate (°F.) |
|---|---|
| Hot: 90°-135° | 20:1 |
| Warm: 70°-99° | 18:1 |
| Cool: 50°-75° | 15:1 |
| Cold: 33°-55° | 13:1 |
| Below Freezing: 0°-37° | 10:1 |
| Arctic: −50°-5° | 8:1 |
| Polar: −100°-−45° | 7:1 |

Table 9 provides the ratio of total lipids to each of monounsaturated, polyunsaturated, and saturated fatty acids in the lipid compositions of this example, for a range of climates. The ratios are presented, for any one of the liquid only, solid only, or combination formulations.

TABLE 9

Ratio of Total Lipids to Specific Lipid Components By Climate

| | Ratios by Climate (° F.) | | | | | | |
|---|---|---|---|---|---|---|---|
| | HOT 90°-135° | WARM 70°-99° | COOL 50°-75° | COLD 33°-55° | BELOW FREEZING 0°-37° | ARCTIC −50°-5° | POLAR −100°-−45° |
| Total Lipids: Monounsaturated Fats | 2.1 | 2.2 | 2.2 | 2.1 | 2.2 | 2.1 | 2.1 |
| Total Lipids: Polyunsaturated Fats | 3.8 | 3.2 | 3.2 | 3.3 | 3.1 | 3.3 | 3.2 |
| Total Lipids: Saturated Fats | 5.0 | 5.4 | 5.5 | 5.7 | 5.9 | 6.1 | 6 |

Example 3

Lipid Compositions Based on Age, Sex and Diet

One aspect of the disclosure is to supply lipid formulation tailored to different human subjects based on their age and sex, and diet. Table 10 below provides dose ranges for total fatty acids content in grams, the ratio range of monounsaturated fatty acids to polyunsaturated fatty acids, and the ratio range of monounsaturated fatty acids to saturated fatty acids, range of omega-6 fatty acids content in grams, ratio range of omega-9 to omega-6 fatty acids, range of omega-3 fatty acids content in grams, and the ratio range of omega-6 to omega-3 fatty acids for vegetarian or high antioxidant and/or high phytochemical consuming non-vegetarian subjects as disclosed by embodiments of the present disclosure, by gender and age group.

TABLE 10

Lipid Dosages Based on Age and Sex for Vegetarians and High Anti-Oxidant/Phytochemical Consuming Omnivores

| | Range Total Fat - g | Range Mono:Poly | Range Mono:Sat | Range O6 - g | Range O9:O6 | Range O3 - g | Range O6:O3 |
|---|---|---|---|---|---|---|---|
| Infants | | | | | | | |
| 7-12 mo | 10-50 | 1:1-3:1 | 1:1-5:1 | 1-10 | 1:1-3:1 | 0.1-3 | 4:1-45:1 |
| Children | | | | | | | |
| 1-3 y | 10-60 | 1:1-3:1 | 1:1-5:1 | 2-15 | 1:1-3:1 | 0.1-3 | 4:1-45:1 |
| Males | | | | | | | |
| 4-8 y | 10-75 | 1:1-3:1 | 1:1-5:1 | 2-25 | 1:1-3:1 | 0.1-4 | 4:1-45:1 |
| 9-13 y | 15-80 | 1:1-3:1 | 1:1-5:1 | 2-30 | 1:1-3:1 | 0.1-4 | 4:1-45:1 |
| 14-18 y | 20-100 | 1:1-3:1 | 1:1-5:1 | 2-35 | 1:1-3:1 | 0.2-5 | 4:1-45:1 |
| 19-30 y | 20-100 | 1:1-3:1 | 1:1-5:1 | 2-40 | 1:1-3:1 | 0.2-5 | 4:1-45:1 |
| 31-50 y | 20-80 | 1:1-3:1 | 1:1-5:1 | 2-40 | 1:1-3:1 | 0.2-5 | 4:1-45:1 |
| 51-70 y | 15-80 | 1:1-3:1 | 1:1-5:1 | 2-30 | 1:1-3:1 | 0.2-5 | 4:1-45:1 |
| >70 y | 15-80 | 1:1-3:1 | 1:1-5:1 | 2-30 | 1:1-3:1 | 0.2-5 | 4:1-45:1 |
| Females | | | | | | | |
| 4-8 y | 12-70 | 1:1-3:1 | 1:1-5:1 | 2-25 | 1:1-3:1 | 0.1-3 | 4:1-45:1 |
| 9-13 y | 15-80 | 1:1-3:1 | 1:1-5:1 | 2-25 | 1:1-3:1 | 0.1-3 | 4:1-45:1 |
| 14-18 y | 20-80 | 1:1-3:1 | 1:1-5:1 | 2-30 | 1:1-3:1 | 0.2-4 | 4;1-45:1 |
| 19-30 y | 20-80 | 1:1-3:1 | 1:1-5:1 | 2-30 | 1:1-3:1 | 0.2-4 | 4:1-45:1 |
| 31-50 y | 15-80 | 1:1-3:1 | 1:1-5:1 | 2-30 | 1:1-3:1 | 0.2-4 | 4:1-45:1 |
| Pregnancy | 24-100 | 1:1-3:1 | 1:1-5:1 | 2-35 | 1:1-3:1 | 0.2-5 | 4:1-45:1 |
| Lactation | 24-100 | 1:1-3:1 | 1:1-5:1 | 2-35 | 1:1-3:1 | 0.2-5 | 4:1-45:1 |
| Menopause | 15-80 | 1:1-3:1 | 1:1-5:1 | 2-30 | 1:1-3:1 | 0.2-4 | 4:1-45:1 |

Table 11 provides dose ranges for total fatty acids content in grams, the ratio range of monounsaturated fatty acids to polyunsaturated fatty acids, and the ratio range of monounsaturated fatty acids to saturated fatty acids, range of omega-6 fatty acids content in grams, ratio range of omega-9 to omega-6 fatty acids, range of omega-3 fatty acids content in grams, and the ratio range of omega-6 to omega-3 fatty acids for non-vegetarian (i.e., omnivorous) or low-antioxidant and/or low phytochemicals consuming vegetarian subjects as disclosed by the present disclosure by gender and age group.

TABLE 11

Lipid Dosages Based on Age and Sex for Omnivores and Low Anti-Oxidant/Phytochemical Consuming Vegetarians

|  | Range Total Fat - g | Range Mono:Poly | Range Mono:Sat | Range O6 - g | Range O9:O6 | Range O3 - g | Range O6:O3 |
|---|---|---|---|---|---|---|---|
| Infants |  |  |  |  |  |  |  |
| 7-12 mo | 10-50 | 1:1-3:1 | 1:1-5:1 | 1-10 | 1:1-3:1 | 0.1-3 | 1:1-10:1 |
| Children |  |  |  |  |  |  |  |
| 1-3 y | 10-60 | 1:1-3:1 | 1:1-5:1 | 2-15 | 1:1-3:1 | 0.1-3 | 1:1-10:1 |
| Males |  |  |  |  |  |  |  |
| 4-8 y | 10-75 | 1:1-3:1 | 1:1-5:1 | 2-20 | 1:1-3:1 | 0.2-5 | 1:1-10:1 |
| 9-13 y | 15-80 | 1:1-3:1 | 1:1-5:1 | 2-25 | 1:1-3:1 | 0.2-5 | 1:1-10:1 |
| 14-18 y | 20-100 | 1:1-3:1 | 1:1-5:1 | 2-30 | 1:1-3:1 | 0.3-6 | 1:1-10:1 |
| 19-30 y | 20-100 | 1:1-3:1 | 1:1-5:1 | 2-35 | 1:1-3:1 | 0.3-6 | 1:1-10:1 |
| 31-50 y | 20-80 | 1:1-3:1 | 1:1-5:1 | 2-35 | 1:1-3:1 | 0.3-6 | 1:1-10:1 |
| 51-70 y | 15-80 | 1:1-3:1 | 1:1-5:1 | 2-25 | 1:1-3:1 | 0.3-6 | 1:1-10:1 |
| >70 y | 15-80 | 1:1-3:1 | 1:1-5:1 | 2-25 | 1:1-3:1 | 0.3-6 | 1:1-10:1 |
| Females |  |  |  |  |  |  |  |
| 4-8 y | 12-70 | 1:1-3:1 | 1:1-5:1 | 2-20 | 1:1-3:1 | 0.2-4 | 1:1-10:1 |
| 9-13 y | 15-80 | 1:1-3:1 | 1:1-5:1 | 2-20 | 1:1-3:1 | 0.2-4 | 1:1-10:1 |
| 14-18 y | 20-80 | 1:1-3:1 | 1:1-5:1 | 2-25 | 1:1-3:1 | 0.3-5 | 1:1-10:1 |
| 19-30 y | 20-80 | 1:1-3:1 | 1:1-5:1 | 2-25 | 1:1-3:1 | 0.3-5 | 1:1-10:1 |
| 31-50 y | 15-80 | 1:1-3:1 | 1:1-5:1 | 2-25 | 1:1-3:1 | 0.3-5 | 1:1-10:1 |
| Pregnancy | 24-100 | 1:1-3:1 | 1:1-5:1 | 2-30 | 1:1-3:1 | 0.3-5 | 1:1-10:1 |
| Lactation | 24-100 | 1:1-3:1 | 1:1-5:1 | 2-30 | 1:1-3:1 | 0.3-5 | 1:1-10:1 |
| Menopause | 15-80 | 1:1-3:1 | 1:1-5:1 | 2-25 | 1:1-3:1 | 0.3-5 | 1:1-10:1 |

Table 12 provides dose ranges for total fatty acids content in grams, the ratio range of mono-unsaturated fatty acids to polyunsaturated fatty acids, and the ratio range of monounsaturated fatty acids to saturated fatty acids, range of omega-6 fatty acids content in grams, ratio range of omega-9 to omega-6 fatty acids, range of omega-3 fatty acids content in grams and the ratio range of omega-6 to omega-3 fatty acids for high-seafood consumers as disclosed by the present disclosure by gender and age group.

TABLE 12

Lipid Dosages Based on Age and Sex for High-Seafood Consumers

|  | Range Total Fat - g | Range Mono:Poly | Range Mono:Sat | Range O6 - g | Range O9:O6 | Range O3 - g | Range O6:O3 |
|---|---|---|---|---|---|---|---|
| Infants |  |  |  |  |  |  |  |
| 7-12 mo | 10-50 | 1:1-3:1 | 1:1-5:1 | 1-10 | 1:1-3:1 | 0.1-3 | 2:1-30:1 |
| Children |  |  |  |  |  |  |  |
| 1-3 y | 10-60 | 1:1-3:1 | 1:1-5:1 | 2-15 | 1:1-3:1 | 0.1-3 | 2:1-30:1 |
| Males |  |  |  |  |  |  |  |
| 4-8 y | 10-75 | 1:1-3:1 | 1:1-5:1 | 2-25 | 1:1-3:1 | 0.1-4 | 2:1-30:1 |
| 9-13 y | 15-80 | 1:1-3:1 | 1:1-5:1 | 2-30 | 1:1-3:1 | 0.1-4 | 2:1-30:1 |
| 14-18 y | 20-100 | 1:1-3:1 | 1:1-5:1 | 2-35 | 1:1-3:1 | 0.2-5 | 2:1-30:1 |
| 19-30 y | 20-100 | 1:1-3:1 | 1:1-5:1 | 2-40 | 1:1-3:1 | 0.2-5 | 2:1-30:1 |
| 31-50 y | 20-80 | 1:1-3:1 | 1:1-5:1 | 2-40 | 1:1-3:1 | 0.2-5 | 2:1-30:1 |
| 51-70 y | 15-80 | 1:1-3:1 | 1:1-5:1 | 2-30 | 1:1-3:1 | 0.2-5 | 2:1-30:1 |
| >70 y | 15-80 | 1:1-3:1 | 1:1-5:1 | 2-30 | 1:1-3:1 | 0.2-5 | 2:1-30:1 |
| Females |  |  |  |  |  |  |  |
| 4-8 y | 12-70 | 1:1-3:1 | 1:1-5:1 | 2-25 | 1:1-3:1 | 0.1-3 | 2:1-30:1 |
| 9-13 y | 15-80 | 1:1-3:1 | 1:1-5:1 | 2-25 | 1:1-3:1 | 0.1-3 | 2:1-30:1 |

TABLE 12-continued

Lipid Dosages Based on Age and Sex for High-Seafood Consumers

|  | Range Total Fat - g | Range Mono:Poly | Range Mono:Sat | Range O 6 - g | Range O9:O6 | Range O3 - g | Range O6:O3 |
|---|---|---|---|---|---|---|---|
| 14-18 y | 20-80 | 1:1-3:1 | 1:1-5:1 | 2-30 | 1:1-3:1 | 0.2-4 | 2:1-30:1 |
| 19-30 y | 20-80 | 1:1-3:1 | 1:1-5:1 | 2-30 | 1:1-3:1 | 0.2-4 | 2:1-30:1 |
| 31-50 y | 15-80 | 1:1-3:1 | 1:1-5:1 | 2-30 | 1:1-3:1 | 0.2-4 | 2:1-30:1 |
| Pregnancy | 24-100 | 1:1-3:1 | 1:1-5:1 | 2-35 | 1:1-3:1 | 0.2-5 | 2:1-30:1 |
| Lactation | 24-100 | 1:1-3:1 | 1:1-5:1 | 2-35 | 1:1-3:1 | 0.2-5 | 2:1-30:1 |
| Menopause | 15-80 | 1:1-3:1 | 1:1-5:1 | 2-30 | 1:1-3:1 | 0.2-4 | 2:1-30:1 |

In some embodiments, the ratio of omega-6 to omega-3 fatty acids is in the range of approximately 1:1 to approximately 50:1, is approximately 1:1, is approximately 2:1, is approximately 3:1, is approximately 4:1, is approximately 5:1, is approximately 6:1, is approximately 7:1, is approximately 8:1, is approximately 9:1, is approximately 10:1, is approximately 11:1, is approximately 12:1, is approximately 15:1, is approximately 20:1, is approximately 25:1, is approximately 30:1, is approximately 35:1, is approximately 40:1, is approximately 45:1, or is approximately 50:1 w/w, w/v, or v/v.

Example 4

Diet Formulations

In one embodiment, the total daily lipids from all foods are within the ratios described herein and the compositions described herein are administered to an individual that falls within the age and calorie intake range as recommended.

In another embodiment, the lipid ratios and compositions described herein are administered to an individual whose total diet comprises 20%-45% of calories from fat (including from the lipid compositions), 45%-65% calories from carbohydrates, and 10%-25% calories from proteins. In one particular aspect, the total calories consumed by the individual falls within the ranges as daily recommended average, as per gender, age, and activity level, to name a few.

In particular embodiments a meal plan may be established for the subject to be followed in conjunction with the administration of the composition.

In some embodiments, the lipid ratios and compositions described herein are administered to an individual whose diet comprises 20%-45% of calories from fat. In one aspect 50-90% of calories from fat are supplied by the lipid compositions described herein. In a further aspect the calories from fats are supplied by one or more of fish oils, dairy products (butter, butter oil, milk, milk cream, and/or cheese), fruit oils, vegetable oils, nuts, seeds, nut oils, and seed oils.

In some embodiments, the lipid ratios and compositions described herein are administered to an individual whose diet comprises 45%-65% of total calories from carbohydrates. In another aspect the diet comprises 45%-65% of total calories from carbohydrates, which carbohydrates are from a 50%-70% intake of grains in calories, 15%-30% intake of vegetables in calories, and 10%-30% intake of fruits in calories. In a related aspect the calories from carbohydrates are additionally from one or more of spices, sweeteners, and beverages. In a further aspect the 50%-70% of carbohydrates from grains are supplied by one or more of wheat, rice, corn, barley, spelt, oats, rye, buckwheat, millet, quinoa, and other grains.

In some embodiments, the lipid ratios and compositions described herein are administered to an individual whose diet comprises 10%-25% of calories from proteins. In another aspect the diet comprises 10%-25% of calories from proteins, which proteins are from one or more of but not limited to legumes, eggs, cheese, milk, yogurt, poultry, seafood, and meat.

In one embodiment, a diet plan is provided which includes the 25%-45% of calories from fat, which are supplied by the lipid compositions described herein. In a related embodiment, a 1-day, a 1-week, a 2-week, or a 1-month diet plan is provided which includes the 20%-45% of calories from fat, of which 50-90% of fat calories are supplied by the lipid compositions described herein. In one diet plan, the remaining 45-65% of calories from carbohydrates and 10-25% of calories from proteins are supplied by a diet including the following components, ranges specified in calories.
  a. Calories from Carbohydrates 45-65%
    i. Grains 50-70%
      1. Wheat<50%
      2. Rice<50%
      3. Corn<20%
      4. Barley<20%
      5. Spelt<20%
      6. Oats<20%
      7. Rye<20%
      8. Buckwheat<15%
      9. Millet<15%
      10. Quinoa<15%
      11. Other Grains<10%
    ii. Vegetables 15-30%
      1. Asparagus, Bell Peppers, Cucumber, Eggplant, Green beans, Green peas, Kale, Romaine, Spinach, Squash summer and winter, Tomato, Carrots, Romaine Lettuce, Radish, Bitter Gourd, Okra, Fenugreek Leaves<50%
      2. Broccoli, Brussels Sprout, Cabbage, Chard, Cauliflower, Mustard Greens, Collard Greens, Turnip Greens<40%
      3. Turnip, Beets, Potatoes, Yams, Sweet Potatoes<50%
      4. Fungi, including mushrooms and yeast<25%
      5. Other Vegetables<15%
    iii. Fruits 10-30%
      1. Apple, Apricot, Orange, Pear, Plum, Banana, Cantaloupe, Grapes<75%
      2. Grapefruit, Papaya, Mango, Pineapple<50%
      3. Blueberries, Cranberries, Figs, Kiwi, Prune, Raspberries, Pomegranate, Strawberries, Watermelon<30%
      4. Other fruits<15%
    iv. Spices<7%
      1. Basil, Black pepper, Cayenne pepper, Chili Pepper, Cinnamon, Cloves, Coriander seeds and leaves, Cumin, Dill, Ginger, Mustard Seeds, Oregano, Peppermint leaves, Rosemary, Sage, Thyme, Turmeric, Fennel, Garlic, Onion, Leeks, Parsley, Celery, Cardamom, Saffron, Lime, Lemon, Tamarind, Mint, Vinegar, other v. Sweeteners<7%
  1. Molasses, Cane Juice, Honey, Maple Syrup, Dates, Raisins, Dried Berries, Figs, Sugar, other vi. Beverages<5%
  1. Green tea, Black tea, Cocal, Coffee, Alcohol, other<5% polyunsaturated fatty acids, and the ratio range of monounsaturated fatty acids to saturated fatty acids, range of omega-6 fatty acids content in grams, ratio range of omega-9 to omega-6 fatty acids, ratio range of omega-6 to omega-3 fatty acids, range of omega-3 fatty acids content in grams designed by age and gender with increasing strength of omega-3, low, medium, and high, such that the human subject may choose the composition most agreeable to his/her diet, where the selection may be based upon the level of antioxidants and phytochemicals in the diet and/or medical predisposition.

TABLE 13

| Lipid Dosages Based on Age and Sex for Various Levels of Omega-3 Fatty Acids | | | | | | | | | |
|---|---|---|---|---|---|---|---|---|---|
| | Range Total Fat - g | Range Mono:Poly | Range Mono:Sat | Range O6 - g | Range O9:O6 | Range O6:O3 | Low Strength Range O3 - g | Med. Strength Range O3 - g | High Strength Range O3 - g |
| Infants | | | | | | | | | |
| 7-12 mo | 10-50 | 1:1-3:1 | 1:1-5:1 | 1-10 | 1:1-3:1 | 1:1-45:1 | 0.1-1.2 | 1.0-2.5 | 2.0-3.0 |
| Children | | | | | | | | | |
| 1-3 y | 10-60 | 1:1-3:1 | 1:1-5:1 | 2-15 | 1:1-3:1 | 1:1-45:1 | 0.1-1.2 | 1.0-2.5 | 2.0-3.0 |
| Males | | | | | | | | | |
| 4-8 y | 10-75 | 1:1-3:1 | 1:1-5:1 | 2-20 | 1:1-3:1 | 1:1-45:1 | 0.1-1.2 | 1.0-2.5 | 2.0-5.0 |
| 9-13 y | 15-80 | 1:1-3:1 | 1:1-5:1 | 2-25 | 1:1-3:1 | 1:1-45:1 | 0.1-1.2 | 1.0-2.5 | 2.0-5.0 |
| 14-18 y | 20-100 | 1:1-3:1 | 1:1-5:1 | 2-30 | 1:1-3:1 | 1:1-45:1 | 0.2-1.2 | 1.0-2.5 | 2.0-6.0 |
| 19-30 y | 20-100 | 1:1-3:1 | 1:1-5:1 | 2-35 | 1:1-3:1 | 1:1-45:1 | 0.2-1.2 | 1.0-2.5 | 2.0-6.0 |
| 31-50 y | 20-80 | 1:1-3:1 | 1:1-5:1 | 2-35 | 1:1-3:1 | 1:1-45:1 | 0.2-1.2 | 1.0-2.5 | 2.0-6.0 |
| 51-70 y | 15-80 | 1:1-3:1 | 1:1-5:1 | 2-25 | 1:1-3:1 | 1:1-45:1 | 0.2-1.2 | 1.0-2.5 | 2.0-6.0 |
| >70 y | 15-80 | 1:1-3:1 | 1:1-5:1 | 2-25 | 1:1-3:1 | 1:1-45:1 | 0.2-1.2 | 1.0-2.5 | 2.0-6.0 |
| Females | | | | | | | | | |
| 4-8 y | 12-70 | 1:1-3:1 | 1:1-5:1 | 2-20 | 1:1-3:1 | 1:1-45:1 | 0.1-1.2 | 1.0-2.5 | 2.0-4.0 |
| 9-13 y | 15-80 | 1:1-3:1 | 1:1-5:1 | 2-20 | 1:1-3:1 | 1:1-45:1 | 0.1-1.2 | 1.0-2.5 | 2.0-4.0 |
| 14-18 y | 20-80 | 1:1-3:1 | 1:1-5:1 | 2-25 | 1:1-3:1 | 1:1-45:1 | 0.2-1.2 | 1.0-2.5 | 2.0-5.0 |
| 19-30 y | 20-80 | 1:1-3:1 | 1:1-5:1 | 2-25 | 1:1-3:1 | 1:1-45:1 | 0.2-1.2 | 1.0-2.5 | 2.0-5.0 |
| 31-50 y | 15-80 | 1:1-3:1 | 1:1-5:1 | 2-25 | 1:1-3:1 | 1:1-45:1 | 0.2-1.2 | 1.0-2.5 | 2.0-5.0 |
| Pregnancy | 24-100 | 1:1-3:1 | 1:1-5:1 | 2-30 | 1:1-3:1 | 1:1-45:1 | 0.2-1.2 | 1.0-2.5 | 2.0-5.0 |
| Lactation | 24-100 | 1:1-3:1 | 1:1-5:1 | 2-30 | 1:1-3:1 | 1:1-45:1 | 0.2-1.2 | 1.0-2.5 | 2.0-5.0 |
| Menopause | 15-80 | 1:1-3:1 | 1:1-5:1 | 2-25 | 1:1-3:1 | 1:1-45:1 | 0.1-1.2 | 1.0-2.5 | 2.0-4.0 | b. Calories from proteins 10-25%
  i. Legumes: Black beans, Dried Peas, Mung beans, Garbanzo, Kidney beans, Lentils, Lima beans, Navy beans, Pinto beans, Soybeans<75%
  ii. Eggs<2.5%
  iii. Cheese<25%
  iv. Milk<25%
  v. Yogurt<25%
  vi. Poultry<30%
  vii. Seafood<30%
  viii. Meat<30%
  ix. Other<15%

Example 5

Formulation with Varied Omega-3 Fatty Acid Content

Table 13 provides dose ranges for total fatty acids content in grams, the ratio range of monounsaturated fatty acids to Example 6

Formulation Based on Medical Conditions

In various embodiments, lipid compositions described herein are administered to an individual for the prophylaxis and/or treatment of diseases, disorders or conditions. For example, the lipid formulation is used to alleviate symptoms of menopause, the process of the cessation of menstruation. It is also used to alleviate the symptoms of endocrine disorders.

Table 14 provides dose ranges for total fatty acids content in grams, the ratio range of monounsaturated fatty acids to polyunsaturated fatty acids, and the ratio range of monounsaturated fatty acids to saturated fatty acids, range of omega-6 fatty acids content in grams, ratio range of omega-9 to omega-6 fatty acids, range of omega-3 fatty acids content in grams, and the ratio range of omega-6 to omega-3 fatty acids for subjects with medical indications as disclosed by the present disclosure.

TABLE 14

Lipid Formulation Based on Medical Conditions

|  | Range Total Fat - g | Range Mono:Poly | Range Mono:Sat | Range O6 - g | Range O9:O6 | Range O3 - g | Range O6:O3 |
|---|---|---|---|---|---|---|---|
| Menopause | 15-100 | 1:1-3:1 | 1:1-5:1 | 2-30 | 1:1-5:1 | 0.2-4 | 1:1-45:1 |
| Cardiovascular Disease | 15-100 | 1:1-3:1 | 1:1-5:1 | 2-35 | 1:1-5:1 | 0.1-6 | 1:1-45:1 |
| Mental Disorders | 15-100 | 1:1-3:1 | 1:1-5:1 | 2-30 | 1:1-5:1 | 0.1-6 | 1:1-45:1 |
| Musculoskelatal Disorders | 15-100 | 1:1-3:1 | 1:1-5:1 | 2-30 | 1:1-5:1 | 0.1-6 | 1:1-45:1 |
| Symptoms of Aging | 15-100 | 1:1-3:1 | 1:1-5:1 | 2-30 | 1:1-5:1 | 0.1-6 | 1:1-45:1 |
| Endocrine Disorders | 15-100 | 1:1-3:1 | 1:1-5:1 | 2-35 | 1:1-5:1 | 0.1-5 | 1:1-45:1 |
| Viral Infections | 15-100 | 1:1-3:1 | 1:1-5:1 | 1-30 | 1:1-5:1 | 0.1-4 | 1:1-45:1 |
| Bacterial Infections | 15-100 | 1:1-3:1 | 1:1-5:1 | 1-30 | 1:1-5:1 | 0.1-4 | 1:1-45:1 |
| Obesity | 15-100 | 1:1-3:1 | 1:1-5:1 | 1-40 | 1:1-5:1 | 0.1-6 | 1:1-45:1 |
| Renal Diseases | 15-100 | 1:1-3:1 | 1:1-5:1 | 1-30 | 1:1-5:1 | 0.1-6 | 1:1-45:1 |
| Pulmonary Disorders | 15-100 | 1:1-3:1 | 1:1-5:1 | 1-25 | 1:1-5:1 | 0.1-6 | 1:1-45:1 |
| Opthalmologic Disorders | 15-100 | 1:1-3:1 | 1:1-5:1 | 1-25 | 1:1-5:1 | 0.1-6 | 1:1-45:1 |
| Dental Disorders | 15-100 | 1:1-3:1 | 1:1-5:1 | 2-30 | 1:1-5:1 | 0.1-6 | 1:1-45:1 |
| Cancer | 15-100 | 1:1-3:1 | 1:1-5:1 | 1-35 | 1:1-5:1 | 0.1-6 | 1:1-45:1 |

Example 7

Lipid Composition According to Diet and Medical Condition

In one example lipid composition parameters were established per diet or medical condition, intended for daily administration (one or more components). As per Table 15 and Table 16 the parameters of the compositions were established for an individual whose diet is high in antioxidants/phytochemicals and/or is a vegetarian; an individual whose diet is low in antioxidants/phytochemicals and/or is a non-vegetarian, or an individual presenting with a medical condition or disorder. The compositions are made up of a variety of nut oils, seed oils, vegetable oils, fruit oils, and other oils, nuts, and seeds. Table 15 presents the ratio ranges of polyunsaturated, monounsaturated, saturated, omega-3, omega-6, and omega-9 fatty acids. Table 16 presents some composition with the specified ratios of polyunsaturated, monounsaturated, saturated, omega-3, omega-6, and omega-9 fatty acids.

TABLE 15

Lipid Composition in Ratio Ranges, by Diet Type or Medical Condition

| | Ratio Ranges by Diet | | | | | |
|---|---|---|---|---|---|---|
| | High Antioxidant/ Phytochemical Diet and/or Vegetarian | | Low Antioxidant/ Phytochemical Diet and/or Non-Vegetarian | | Individual with Medical Issues | |
| | Low | High | Low | High | Low | High |
| Total Lipids: Monounsaturated Fats | 1.50 | 4.00 | 1.50 | 4.00 | 1.50 | 4.00 |
| Monounsaturated: Polyunsaturated Fats | 1.00 | 3.00 | 1.00 | 3.00 | 1.00 | 3.00 |
| Polyunsaturated: Saturated Fats | 1.00 | 3.00 | 1.00 | 3.00 | 1.00 | 3.00 |
| Monounsaturated: Saturated Fats | 1.00 | 4.00 | 1.00 | 4.00 | 1.00 | 4.00 |
| O9:O6 | 1.00 | 3.00 | 1.00 | 3.00 | 1.00 | 5.00 |
| O6:O3 | 4.00 | 20.00 | 1.00 | 8.00 | 1.00 | 20.00 |
| O9:O3 | 5.00 | 30.00 | 4.00 | 10.00 | 4.00 | 10.00 |
| O9 % of Total Lipids | 22.86 | 91.43 | 21.62 | 86.49 | 22.86 | 91.43 |
| O6 % of Total Lipids | 12.86 | 51.43 | 10.81 | 43.24 | 5.71 | 22.86 |
| O3 % of Total Lipids | 0.86 | 3.43 | 4.05 | 16.22 | 5.71 | 22.86 |

TABLE 16

Lipid Composition Ratios, by Diet Type or Medical Condition

| Ratios | High Antioxidant/ Phytochemical Diet and/or Vegetarian | Low Antioxidant/ Phytochemical Diet and/or Non-Vegetarian | Individual with Medical Issues |
|---|---|---|---|
| Total Lipids: Monounsaturated Fats | 2.19 | 2.31 | 2.19 |
| Monounsaturated: Polyunsaturated Fats | 1.45 | 1.23 | 1.45 |
| Polyunsaturated: Saturated Fats | 1.38 | 1.63 | 1.38 |
| Monounsaturated: Saturated Fats | 2.00 | 2.00 | 2.00 |
| O9:O6 | 1.78 | 2.00 | 4.00 |
| O6:O3 | 15.00 | 2.67 | 1.00 |
| O9:O3 | 26.67 | 5.33 | 4.00 |
| O9 % of Total Lipids | 45.71 | 43.24 | 45.71 |

TABLE 16-continued

Lipid Composition Ratios, by Diet Type or Medical Condition

| Ratios | High Antioxidant/ Phytochemical Diet and/or Vegetarian | Low Antioxidant/ Phytochemical Diet and/or Non-Vegetarian | Individual with Medical Issues |
|---|---|---|---|
| O6 % of Total Lipids | 25.71 | 21.62 | 11.43 |
| O3 % of Total Lipids | 1.71 | 8.11 | 11.43 |

Example 8

Two-Component Lipid Formulation According to Diet and Medical Condition

In one example liquid lipid and solid lipid composition parameters were established per diet or medical condition, intended for twice-a-day administration (i.e. 2 component daily formulation). As per Table 17 to Table 20, the parameters of the compositions were established for an individual whose diet is high in antioxidants/phytochemicals and/or is a vegetarian; an individual whose diet is low in antioxidants/phytochemicals and/or is a non-vegetarian, or an individual presenting with a medical condition or disorder. The compositions are made up of a variety of nut oils, seed oils, vegetable oils, fruit oils, and other oils, nuts, and seeds. Table 17 presents the ratios of polyunsaturated, monounsaturated, saturated, omega-3, omega-6, and omega-9 fatty acids for the bar (solid) formulation. Table 18 presents the ratios of polyunsaturated, monounsaturated, saturated, omega-3, omega-6, and omega-9 fatty acids for the liquid formulation. Table 19 presents examples of bar formulation (solid) and Table 20 presents one liquid composition with the specified ratio ranges of polyunsaturated, monounsaturated, saturated, omega-3, omega-6, and omega-9 fatty acids.

TABLE 17

Solid Lipid Composition in Ratios, by Diet Type or Medical Condition

| 2-Component Formulation, Ratios Ratios | In Bar Formulation | | |
|---|---|---|---|
| | High Antioxidant/ Phytochemical Diet and/or Vegetarian | Low Antioxidant/ Phytochemical Diet and/or Non-Vegetarian | Individual with Medical Issues |
| Total Lipids: Monounsaturated Fats | 2.33 | 2.56 | 2.40 |
| Monounsaturated: Polyunsaturated Fats | 1.50 | 1.13 | 1.25 |
| Polyunsaturated: Saturated Fats | 1.00 | 1.33 | 1.33 |
| Monounsaturated: Saturated Fats | 1.50 | 1.50 | 1.67 |
| O9:O6 | 1.33 | 1.33 | 1.60 |
| O6:O3 | 10.00 | 3.00 | 2.50 |
| O9:O3 | 13.33 | 4.00 | 4.00 |
| Omega-9 % of Total Lipids | 38.10 | 34.78 | 33.33 |
| Omega-6 % of Total Lipids | 28.57 | 26.09 | 20.83 |
| Omega-3 % of Total Lipids | 2.86 | 8.70 | 8.33 |

TABLE 18

Liquid Lipid Composition in Ratios, by Diet Type or Medical Condition

| 2-Component Formulation, Ratios Ratios | In Liquid Formulation | | |
|---|---|---|---|
| | High Antioxidant/ Phytochemical Diet and/or Vegetarian | Low Antioxidant/ Phytochemical Diet and/or Non-Vegetarian | Individual with Medical Issues |
| Total Lipids: Monounsaturated Fats | 1.87 | 2.00 | 2.25 |
| Monounsaturated: Polyunsaturated Fats | 1.67 | 1.36 | 1.00 |
| Polyunsaturated: Saturated Fats | 2.25 | 2.75 | 4.00 |
| Monounsaturated: Saturated Fats | 3.75 | 3.75 | 4.00 |
| O9:O6 | 1.72 | 1.75 | 2.00 |
| O6:O3 | 41.60 | 4.00 | 2.00 |
| O9:O3 | 71.50 | 7.00 | 4.00 |
| Omega-9 % of Total Lipids | 51.07 | 46.67 | 44.44 |
| Omega-6 % of Total Lipids | 29.71 | 26.67 | 22.22 |
| Omega-3 % of Total Lipids | 0.71 | 6.67 | 11.11 |

TABLE 19

Solid Lipid Composition in Ratio Ranges, by Diet Type or Medical Condition

| 2-Component Formulation, Ratio Ranges | Bar Formulation | | | | | |
|---|---|---|---|---|---|---|
| | High Antioxidant/ Phytochemical Diet and/or Vegetarian | | Low Antioxidant/ Phytochemical Diet and/or Non-Vegetarian | | Individual with Medical Issues | |
| | Low | High | Low | High | Low | High |
| Total Lipids: Monounsaturated Fats | 1.50 | 4.00 | 1.50 | 4.00 | 1.50 | 4.00 |
| Monounsaturated: Polyunsaturated Fats | 1.00 | 3.00 | 1.00 | 3.00 | 1.00 | 3.00 |

TABLE 19-continued

Solid Lipid Composition in Ratio Ranges, by Diet Type or Medical Condition

| | Bar Formulation | | | | | |
|---|---|---|---|---|---|---|
| | High Antioxidant/ Phytochemical Diet and/or Vegetarian | | Low Antioxidant/ Phytochemical Diet and/or Non-Vegetarian | | Individual with Medical Issues | |
| 2-Component Formulation, Ratio Ranges | Low | High | Low | High | Low | High |
| Polyunsaturated: Saturated Fats | 1.00 | 3.00 | 1.00 | 3.00 | 1.00 | 3.00 |
| Monounsaturated: Saturated Fats | 1.00 | 4.00 | 1.00 | 4.00 | 1.00 | 4.00 |
| O9:O6 | 1.00 | 3.00 | 1.00 | 3.00 | 1.00 | 5.00 |
| O6:O3 | 4.00 | 16.00 | 1.00 | 8.00 | 1.00 | 16.00 |
| O9:O3 | 5.00 | 20.00 | 4.00 | 10.00 | 4.00 | 10.00 |
| Omega-9 % of Total Lipids | 19.05 | 76.19 | 17.39 | 69.57 | 16.67 | 66.67 |
| Omega-6 % of Total Lipids | 14.29 | 57.14 | 13.04 | 52.17 | 10.42 | 41.67 |
| Omega-3 % of Total Lipids | 1.43 | 5.71 | 4.35 | 17.39 | 4.17 | 16.67 |

TABLE 20

Liquid Lipid Composition in Ratio Ranges, by Diet Type or Medical Condition

| | Liquid Formulation | | | | | |
|---|---|---|---|---|---|---|
| | High Antioxidant/ Phytochemical Diet and/or Vegetarian | | Low Antioxidant/ Phytochemical Diet and/or Non-Vegetarian | | Individual with Medical Issues | |
| 2-Component Formulation, Ratio Ranges | Low | High | Low | High | Low | High |
| Total Lipids: Monounsaturated Fats | 1.50 | 4.00 | 1.50 | 4.00 | 1.50 | 4.00 |
| Monounsaturated: Polyunsaturated Fats | 1.00 | 3.00 | 1.00 | 3.00 | 1.00 | 3.00 |
| Polyunsaturated: Saturated Fats | 1.00 | 3.00 | 1.00 | 3.00 | 1.00 | 4.00 |
| Monounsaturated: Saturated Fats | 1.00 | 4.00 | 1.00 | 4.00 | 1.00 | 4.00 |
| O9:O6 | 1.00 | 3.00 | 1.00 | 3.00 | 1.00 | 5.00 |
| O6:O3 | 8.00 | 45.00 | 1.00 | 8.00 | 1.00 | 45.00 |
| O9:O3 | 10.00 | 75.00 | 4.00 | 10.00 | 4.00 | 10.00 |
| Omega-9 % of Total Lipids | 25.54 | 90 | 23.33 | 93.33 | 22.22 | 88.89 |
| Omega-6 % of Total Lipids | 14.86 | 59.43 | 13.33 | 53.33 | 11.11 | 44.44 |
| Omega-3 % of Total Lipids | 0.36 | 1.43 | 3.33 | 13.33 | 5.56 | 22.22 |

Example 9

Special Formulations Based on Diet

In this example one liquid lipid composition parameters was established and one formulation was prepared, intended for once, twice, or thrice or more a day administration to an individual whose diet is high in antioxidants/phytochemicals and/or is a vegetarian and to an individual who does not favor, or cannot tolerate nuts and seeds. The compositions include a variety of nut oils, seed oils, vegetable oils, fruit oils, and other oils. Some ranges for a formulation are provided by % by weight (w/w) for each component (representing the % weight for that individual component on a daily basis). The compositions can be administered once or more daily. Some compositions may include two or more of: almond oil (4%-23%), anhydrous butter oil (5%-29%), avocado oil (%-6%), cashew oil (2%-5%), coconut oil (0%-2%), corn oil (3%-19%), fish oil (0%-5%), flaxseed oil (0%-5%), mustard oil (0%-5%), olive oil (3%-17%), palm oil (0%-5%), peanut oil (5%-30%), pistachio oil (1%-7%), pumpkin seed oil (1%-8%), safflower oil (high oleic) (1%-5%), sesame seed oil (0%-5%), soybean lecithin (0%-5%), soybean oil (1%-7%), sunflower oil (high oleic) (2%-14%), sunflower oil (regular) (0%-5%), and/or walnut oil (3%-15%).

Another set of parameters for one liquid lipid composition was established, intended for once, twice, or thrice a day administration to an individual who does not favor, or can not tolerate nuts and seeds. The compositions included a variety of nut oils, seed oils, vegetable oils, fruit oils, and other oils. Some ranges for a formulation are provided by % by weight (w/w) for each component (representing the % weight for that individual component on a daily basis). The ranges can accommodate vegetarian/high-antioxidant/high-phytochemical user and omnivore/low-antioxidant/low-phytochemical user or a seafood user, in different combinations. The compositions can be administered once or more daily. Some compositions may include two or more of: almond oil (2%-36%), anhydrous butter oil (2%-36%), coconut oil (0%-8%), corn oil (1%-24%), flaxseed oil (0%-8%), mustard oil (0%-8%), olive oil (2%-36), palm oil (0%-2%), peanut oil (4%-72%), pumpkin seeds oil (1%-24%), safflower oil (high oleic) (2%-60%), soybean lecithin (0%-4%), sunflower oil (high oleic) (4%-72%), and/or walnut oil (2%-36%).

Example 10

Daily Formulations

Liquid lipid and solid lipid composition parameters were established for a twice-daily administration (i.e. 2-component daily formulations). The compositions were made up of a variety of nut oils, seed oils, vegetable oils, fruit oils, and other oils. The ranges for each component of the liquid and solid formulations are presented for each of the solid and liquid formulations. The solid formulation includes two or more of by % weight of total composition: almonds (10%-25%), cashews (7%-15%) coconut shredded (1%-4%), flaxseed (0%-1%), olives (15%-25%), peanuts (4%-15%), pistachios (2%-9%), pumpkin seeds (2%-12%), sesame (0%-10%), soybeans (8%-20%), sunflower seeds (1%-4%), and/or walnuts (5%-15%). The liquid formulation includes two or more of by % weight of total composition: avocado oil (3%-14%), corn oil (15%-30%), mustard oil (0%-2%), olive oil (10%-22%), palm oil (0%-2%), peanut oil (15%-35%), safflower oil (high oleic) (5%-15%), soybean lecithin (0%-2%), sunflower oil (high oleic) (10%-25%), and/or anhydrous butter oil (5%-15%).

Some parameters were also established for one or more daily administration (e.g., 1, 2 or 3 component daily formulation). The compositions were made up of a variety of nuts, seeds, nut oils, seed oils, vegetable oils, fruit oils, and other oils. The ranges for each component of the formulations are presented for each of the solid and liquid components. The formulation can include two or more of by % weight of total composition: peanuts or peanut oil (4-35), almonds or almond oil (2%-25%), olives or olive oil (3%-45%), legumes or grains (15%-45%), cashews or cashew oil (10%-40%), pistachios or pistachio oil (5%-25%), pumpkin seeds or pumpkin seed oil (4%-25%), sunflower seeds or sunflower seed oil (2%-30%), sesame seeds or sesame seed oil (0%-20%), walnuts or walnut oil (5%-25%), flaxseed or flaxseed oil (0%-10%), anhydrous butter oil or milk product including cheese (5%-45%), coconut meat or coconut oil (2%-8%), corn oil (3%-20%), avocado oil (3%-8%), safflower oil (2%-20%), mustard oil (0%-8%), palm oil (0%-8%), and/or soybean lecithin (0%-2%).

Example 11

A Case Study on Menopause, Aging, and Musculoskeletal Disorders

A 47-year old female presented with menopause-related hot flushes. The subject's diet was supplemented with a combination of vegetable oils, seed oils, nuts and seeds for a period of 6 weeks. The subject was provided with the twice-daily administration formulation in Example 10. By optimizing omega-6 and omega-3 fatty acids and ratios in the context of the compositions, it was observed that there was an adaptation period over which the intensity of hot flushes gradually diminished. Other symptoms reduced were: night sweats, loss of libido, vaginal dryness, fatigue, hair loss, sensitivity to hot and cold, sleep disorders, difficulty concentrating, memory lapses, weight gain, bloating, mood swings, depression, anxiety, irritability, breast tenderness, migraines, aching joints, burning tongue, the feeling of electric shocks, digestive problems, gum problems, muscle tensions, itchy skin, and tingling in the extremities, as reported by the subject. During the 6-week course of treatment, the subject did improve her posture, which is indicative of greater muscle mass, joint and/or tendon strength and flexibility, and bone density. The effect on osteoporosis can be tested by continuing the treatment with the supplement of oils, nuts, and seeds over a longer period of time and measuring bone density, using standard methods, before, during, and after treatment.

It is likely that beneficial effects of treatment on the menopause-related symptoms was due to achieving steady sex-hormone-like benefit from omega-6 and omega-3 fatty acid supplementation and optimization in the context of antioxidants and phytochemcials. The amount of dietary fat, its composition, and the period during which the nutrient is fed to animals is known to affect the secretion and metabolism of androgens and endogenous steroids, and the presentation of sex hormone receptor on the cell surface. Estrogens and polyunsaturated fatty acids are also believed to have similar actions. In addition to amount and composition, relatively steady dosages may also be important to reduce hormone fluctuations. Das UN. Estrogen, statins, and polyunsaturated fatty acids: similarities in their actions and benefits—is there a common link? Nutrition. 2002 Feb.; 18(2): 178-88. McVey M J, Cooke G M, Curran I H, Chan H M, Kubow S, Lok E, Mehta R. Epub 2007 Sep. 11. Effects of dietary fats and proteins on rat testicular steroidogenic enzymes and serum testosterone levels. Food Chem Toxicol. 2008 January; 46(11):259-69. Gromadzka-Ostrowska J. Effects of dietary fat on androgen secretion and metabolism. Reprod Biol. 2006; 6 Suppl 2:13-20.

Nutrients from the total diet (natural sources) including the lipid composition administered were as follows in Table 21.

TABLE 21

The Subject's Daily Nutrients

| Nutrient | Weight |
|---|---|
| Protein g | 60-100 |
| Carbohydrate g | 225-325 |
| Total Lipids g | 50-65 |
| Calories | 1700-1900 |
| Cholestrol mg | 150-300 |
| Fiber g | 30-45 |
| Alpha Carotene mcg | 3000-4000 |
| Beta Carotene mcg | 10000-14000 |
| Beta Cryptoxanthin mcg | 600-850 |
| Betaine mg | 20-50 |
| Choline mg | 150-250 |
| Folate mcg | 500-800 |
| Lycopene mcg | 1600-1900 |
| Lutein Zeaxanthin mcg | 10000-14000 |
| Niacin mg | 15-20 |
| Pantothenic Acid mg | 8-14 |
| Retinol mcg | 300-400 |
| Riboflavin mg | 2-3 |
| Thiamin mg | 1.5-2.5 |
| Vitamin E Tocopherol Beta mg | 0.1-0.5 |
| Vitamin E Tocopherol Delta mg | 0.1-0.5 |
| Vitamin E Tocopherol Gamma mg | 2.0-4.0 |
| Vitamin E Tocopherol Alpha mg | 10-15 |
| Vitamin A IU | 20000-30000 |
| Vitamin A RAE | 1500-1900 |
| Vitamin B6 mg | 1.5-2.5 |
| Vitamin B12 mcg | 2-5 |
| Vitamin C mg | 250-400 |
| Vitamin D IU | 200-400 |
| Vitamin K mcg | 300-550 |
| Calcium mg | 1200-1500 |

TABLE 21-continued

The Subject's Daily Nutrients

| Nutrient | Weight |
| --- | --- |
| Copper mg | 2-3 |
| Iron mg | 14-18 |
| Magnesium mg | 400-700 |
| Manganese mg | 6-8 |
| Phosphorous mg | 1600-1900 |
| Potassium mg | 3800-5500 |
| Selenium mcg | 65-80 |
| Sodium mg | 2000-2500 |
| Zinc mg | 10-14 |
| Alanine g | 2.5-4.5 |
| Arginine g | 3-4.5 |
| Aspartic acid g | 6-8 |
| Cystine g | 1-2.5 |
| Glutamic acid g | 12-14 |
| Glycine g | 2-4 |
| Histidine g | 1-3 |
| Isoleucine g | 2-4.5 |
| Leucine g | 4.5-7.5 |
| Lysine g | 4-5.5 |
| Methionine g | 1-2.5 |
| Phenylalanine g | 2.5-4.5 |
| Proline g | 4-6 |
| Serine g | 2.5-5.5 |
| Threonine g | 2-4 |
| Tryptophan g | 0.5-2 |
| Tyrosine g | 2-4 |
| Valine g | 3-5 |
| Total Fat g | 50-65 |
| Monounsaturated g | 18-25 |
| Polyunsaturated g | 12-16 |
| Saturated g | 12-15 |
| Butyric acid 4:0 g | 0.2-.75 |
| Caproic acid 6:0 g | 0.1-0.5 |
| Caprylic acid 8:0 g | 0.1-0.5 |
| Caprice acid 10:0 g | 0.2-0.6 |
| Lauric acid 12:0 g | 0.4-0.75 |
| Myristic 14:0 g | 1-3.0 |
| Palmitic 16:0 g | 3.0-7.0 |
| Palmitoleic 16:1 g | 0.25-1.5 |
| Stearic 18:0 g | 1.5-3.0 |
| Oleic 18:1 g | 16-22 |
| Linoleic 18:2 g | 11-14 |
| Alpha-linolenic 18:3 g | 0.8-1.5 |
| Arachidic 20:0 g | 0.1-1.0 |
| Gadoleic (Eicosenoic) 20:1 g | 0.1-.4 |
| Arachidonic 20:4 g | 0.01-0.5 |
| Eicosapentaenoic 20:5 g | 0-0.5 |
| Erucic 22:1 g | 0-0.3 |
| Docosapentaenoic 22:5 g | 0-0.5 |
| Docosahexaenoic 22:6 g | 0.01-0.2 |
| Phytosterols mg | 90-150 |
| Campesterol mg | 0.8-1.5 |
| Sitosterol mg | 15-30 |
| Stigmasterol mg | 0.3-1.5 |

Example 12

A Case Study on Hypercholesterolemia, Cardiovascular Disease

The host subject experienced hypercholesterolemia on a vegetarian diet low in fat, mostly olive oil (75% monounsaturated fat), a daily fish oil supplement of 1 gram, and a daily total essential fatty acids (EFA) supplement of 1 gram. As part of the treatment, the fish oil and EFA supplements were discontinued. The subject was then administered a daily lipid composition supplement containing 11 grams of omega-6 and 1.2 grams of omega-3 fatty acids, made up primarily from a combination of vegetable oils, and nuts and seeds. Administration of the lipid composition resulted in a reduction of LDL from 160 mg to 120 mg. Very low levels of blood pressure were observed, 90/55 mmHg, when omega-3 were increased to 1.8 grams; blood pressure levels normalized at 105/70 mmHg at 11 grams of omega-6 and 1.2 grams of omega-3 fatty acids. When omega-3 were reduced from 1.8 grams to 1.2 grams per day, the subject experienced an irregular heartbeat, which subsided over a period of 2-3 weeks. However, when omega-3 were further reduced to 0.5 grams per day, it resulted in an ongoing arrhythmia.

This case study demonstrated that supplementation with vegetable oils, nuts, and seeds, wherein the omega-6 to omega-3 fatty acids ratio was about 9:1 may result in a significant decrease in LDL cholesterol blood levels (dyslipidemia which is associated with atherosclerosis). This case study also demonstrated that the lipid compositions and ratios described herein may be useful in moderating blood pressure and arrhythmia.

In another human subject, intense muscle spasms arising from the left thoracic cavity/wall were observed subsequent to a meal high in omega-6 fatty acids, whereas the subject's typical diet included primarily monounsaturated fatty acids and very small amounts of saturated fatty acids. It is hypothesized, that sudden increase in omega-6, when the body is chronically deficient may be harmful.

Polyunsaturated fatty acids (omega-3 and omega-6, particularly gamma-linolenic acid) have often been recommended to reduce coronary heart disease along with recommendations to reduce saturated fatty acids. But all saturated fats do not have the same effect on cholesterol synthesis in the liver. Saturated fats of chain-length 12, 14 and 16 (lauric acid, myristic acid and palmitic acid) have been shown to elevate blood cholesterol. Stearic acid (18-carbon, saturated) has been shown to lower cholesterol by 21%—even more than oleic acid (18-carbon, monounsaturated), which lowers LDL by 15%. Polyunsaturated fatty acids increase cell membrane fluidity and therefore tissue flexibility, including that of the arteries. It has been suggested that reduced activity of Delta6 and Delta5 desaturases, enzymes that metabolize essential fatty acids may be a factor in the initiation and progression of atherosclerosis. A defect in the activity of Delta6 and Delta5 desaturases may be a factor in the initiation and progression of atherosclerosis. Prostaglandins Leukot Essent Fatty Acids. 2007 May; 76(5):251-68. Epub 2007 Apr. 26. However, certain phytochemicals have been shown to inhibit the enzymatic activity. Fujiyama-Fujiwara Y, Umeda R, Igarashi O. Effects of sesamin and curcumin on delta 5-desaturation and chain elongation of polyunsaturated fatty acid metabolism in primary cultured rat hepatocytes. J Nutr Sci Vitaminol (Tokyo). 1992 August; 38(4):353-63.

Example 13

A Case Study on Mood Swing, Mental Function

The subject host was placed on a trial of varying ratios of omega-6 and omega-3 fatty acids using various oils and nut combinations. Each time omega-3 were reduced or omega-6 were increased the subject became depressed and was given to crying at the slightest provocation. When omega-3 were increased, it elevated the subject's mood, immediately noticeable. However, within certain ranges of omega-6 and omega-3, the effect was self-adjusting, e.g., over a period of 3-6 weeks the moods normalized. It was also observed that within that range of omega-6 and omega-3 fatty acids, over a period of 3-6 weeks the subject in fact was more grounded at higher levels of omega-6; and was euphoric at higher levels of omega-3. Omega-3 increase enhanced cognitive function, which was immediately noticeable. Omega-3 reduction caused confusion, dyslexia, and a decline in cognitive function but these symptoms subsided with time, again within certain omega-6 and omega-3 fatty acids ranges. The subject also displayed greater attention span and concentration after omega-6 and omega-3 were optimized over a period of 3-6 weeks, with greater reading speeds and comprehension. Thus, the subject performed better at a lower level of omega-3 fatty acids, which suggests that an adaptation mechanism was activated to compensate for the required level of omega-6 metabolites at higher level of dietary omega-3 fatty acids. There may be a similar adaptation mechanism for required level of omega-3 metabolites, when inadequately supplied from the diet. The cumulative effects of such adaptations could pose a threat to the individual in the long run.

Manipulation of dietary fats can alter the fatty acid composition of brain-cell membranes, with effects on thought processing and behavior. Polyunsaturated fatty acids could be associated at different levels in the pathophysiology of major depression, on one hand through their role in the membrane fluidity which influences diverse steps of neurotransmission and, on the other hand, through their function as precursors of pro-inflammatory cytokines and eicosanoids disturbing neurotransmission. Though harmful in excess, cytokines and lipid peroxidation products may exert beneficial effects at low levels. Some studies have found lessened lipid per-oxidation in Attention-Deficit Hyperactivity Disorder among children, suggesting the need to balance lipids with respect to antioxidants. Spahis S et al. "Lipid profile, fatty acids composition and pro- and anti-oxidant status in pediatric patients with attention-deficit/hyperactivity disorder." Prostaglandins Leukot Essent Fatty Acids. 2008 Jul.-Aug.: 79(1-2); 47-53. Epub 2008 Aug. 30.

Example 14

Case Studies on Neural Disorders

1. Progressive Supra-Nuclear Palsy

The subject host was a 50-year old woman whose symptoms included dental sensitivity, deteriorating muscle mass, occasional breathing difficulty, easy bruising, mild arrhythmia, and difficult bowel movement. A dentist, as a solution to her sensitive teeth, had extracted and replaced her teeth with dentures at 50. Each of her other symptoms was treated as a stand-alone symptom and treated with non-lipid medications. At 60 she developed loss of balance, diplopia (double vision), and slurry speech. Eventually when she started having bone-shattering falls, she was diagnosed with Progressive Supra-nuclear Palsy (PSP), a neurological disease mainly characterized by loss of neural tissue in the brainstem. The subject then lost ambulation and speech, and developed dysphagia. She passed away at 67 from pneumonia.

The woman had had four healthy deliveries, a healthy life until 50, and had no incidence of neural disease in her family. Closer examination of changes in her life around 50 revealed that around that time the fats in her diet had been significantly cut back because of the prevalent doctrine in the 1980s that fats cause heart-disease, and that all fats are deleterious. Both of the woman's parents in their early 70s, and a brother at 48, had died of myocardial infarctions. Hence, the fat reduction was a precautionary measure to avoid cardiac disease, which was then believed to have a strong genetic component. However, it is hypothesized in the present disclosure that the fats were cut to a point where she became severely deficient in both omega-6, and omega-3 fatty acids. The woman was a postmenopausal vegetarian with high antioxidant and phytochemicals intake, and the little fat that was in her diet was either saturated fat (less than 20% of total fat) or monounsaturated fat (70-90% of total fat), mostly olive oil following the then doctrine that held olive oil above all others. Olive oil is 75% monounsaturated oil and rich in polyphenols. Since all fatty acids compete in the metabolic pathway and antioxidants and phytochemicals increase the requirement for omega-6, in her case the deficiency of omega-6 acid appears to be the culprit. The deficiency of omega-6 is also evident from her early symptoms: muscle mass requires a balance of omega-6 and omega-3, lack of omega-6-derivative leukotrienes may lead to asthma-like breathing issues (conversely excessive leukotrienes can also lead to asthma like symptoms), deficiency of omega-3 has been linked with arrhythmia, and deficiency of omega-6 derived thromboxanes may lead to easy bruising, and lack of omega-6 derived prostaglandins may impede smooth muscle activity and therefore the bowel movement. The fact that she was post-menopausal made the requirement of omega-6 and omega-3 more critical, since estrogen and androgens, as hypothesized in the present disclosure, have similar actions and benefits as polyunsaturated fats. When the reproductive hormones decline, the body may increasingly depend on omega-6 and omega-3 fatty acids and their metabolites for the physiological functions.

It is an embodiment of the present disclosure, that deficiency of Linoleic acid (LA) metabolite Arachidonic acid (AA) and Alpha-linolenic acid (ALA) metabolite Docosahexaenoic acid (DHA), that are so abundantly present in neural tissue, particularly the membranes of neural synapses, may have caused the neurodgeneration. Neuroinflammation is a host defense mechanism associated with neutralization of an insult and restoration of normal structure and function of brain, and is characteristic of all major neural diseases. The dietary deficiency of LA and ALA, and the resulting unfavorable tissue ratio of AA to DHA might have affected the neurodegeneration associated with acute neural trauma and neurodegenerative disease.

It is important to note that not all omega-6 or omega-3 fatty acids deficiencies or imbalance lead to PSP. It simply creates a distress in the body; the disease developed depends on rest of the body chemistry. In the Western world omega-3 fatty acids have received much attention because the populace's consumption was highly skewed towards omega-6 and that with inadequate antioxidant and phytochemical intake. Requirement of omega-3 may be very small, and may increase only with the increase in omega-6. Disclosed herein are methods and compositions to balance omega-3 and omega-6 fatty acids, in light of demographic factors, and for their steady delivery.

2. Amyotrophic Lateral Sclerosis

The subject was a vegetarian woman in her mid-30s, on a low fat diet using primarily olive oil and nuts. She had developed Amyotrophic Lateral Sclerosis (ALS)-like symptoms: muscle weakness in hands, arms, legs, and the muscles of speech, twitching and cramping of muscles, shortness of breath, and difficulty in swallowing. The left side of her body was affected more than the right side. Upon administration of a lipid composition and changes in diet that increased omega-6 fatty acids to about 12 grams, her symptoms disappeared and the muscle tone improved, better than before the onset of symptoms. It is hypothesized that in this instance, the amount of omega-3 relative to omega-6 in the tissue had exceeded the ratio tolerated by the body. Since the vegetarian diet and nuts contributed plenty of antioxidants and phytochemicals, the subject might have become deficient in omega-6 fatty acids and the required metabolites, despite moderate levels of dietary omega-3 fatty acids.

The initial symptoms of ALS can be quite varied in different people. One person may experience tripping over carpet edges, another person may have trouble lifting and a third person's early symptom may be slurred speech. In a small number of people, ALS is known to remit or halt its progression, though there is no scientific understanding as to how and why this happens. It is hypothesized herein that it has to do with inadvertent change in omega-6 and omega-3 fatty acids consumption. Most of us fall into certain food patterns based on likes and dislikes, habits inherited from family, accessibility of certain foods, cooking habits, and the foods that happen to be in vogue. But, there is always that change in life, a dinner party at a friend's, food gift from a well-wisher, or a vacation to a remote locale, or a new oil that one takes a liking to, which brings about change in diet. All it takes is a handful of nuts, or a spoonful of high-omega-6 and/or omega-3 oil to tip the balance, even if temporarily. However little, it does register in the body.

Subsequent to the experimental adjustment of omega-6 and omega-3 fatty acids levels in other host subjects through the disclosed compositions, improvement in motor coordination, handwriting, balance, and body's ability to follow a rhythm, in dance steps, for example, were observed.

Example 15

Case Studies on Musculoskeletal Disorders

1. Muscular Performance

In a host subject many musculoskeletal issues appeared and disappeared during the course of omega-6 and omega-3 fatty acids therapy through the administration of lipid compositions. Increases in omega-3 beyond 0.5 g, in a vegetarian host with omega-6 at 10-11 grams, yielded better muscular performance, lesser joint pain, lesser joint crackling sounds, and better spatial task performance. But a point of diminishing marginal returns was reached at about 1.2 grams of omega-3. Increases of omega-3 beyond 1.2 grams resulted in weaker muscle tone, posture, and exercise endurance. When the omega-3 was gradually brought back to 1.2 grams, the subject experienced leg cramps, lower back pain, burning sensation in the scalp, buckling of knee joints, and joint pains in knees and shoulders. Over a period of 3-6 weeks these symptoms subsided.

2. Gout

Another host subject developed Gout, a joint disorder, on a low-fat diet, primarily olive oil, and nuts. The symptoms disappeared upon increase of omega-6 in the diet.

3. Myofascial Pains and Thoracic Outlet Syndrome

In a 35-year old vegetarian female, on a low-fat diet using olive oil as the main fat in the diet, the development of episodes of acute myofascial pains were observed. The subject experienced severe muscle tightness in several areas of the body, neck shoulders, para-spinal muscles, thighs, hands, and arms.

The host was diagnosed with Myofascial Pain Syndrome (MFS) and Thoracic Outlet Syndrome (TOS). TOS consists of a group of distinct disorders that affect the nerves in the brachial plexus (nerves that pass into the arms from the neck) and the subclavian artery and vein blood vessels between the base of the neck and axilla (armpit). For the most part, these disorders are produced by compression of the components of the brachial plexus (the large cluster of nerves that pass from the neck to the arm), the subclavian artery, or the subclavian vein. Neurogenic form of TOS accounts for 95-98% of all cases of TOS, hence neural disease was suspected. The host subject went through numerous examinations including: MRIs of the entire CNS, X-rays, blood work, drug therapies, massage therapies, and chiropractic treatment. The symptoms would go away and then reappear a few months or a year later. After omega-6 and omega-3 in the subject's diet were optimized by administration of the disclosed lipid compositions the episodes of TOS and myofascial pains subsided. It is hypothesized herein that these episodes were the result of the body being severely deficient in omega-6 and omega-3 fatty acids. Each time there was an inadvertent increase in omega-6 and omega-3 fatty acids, more particularly omega-6 fatty acids, which can occur by any incidental changes in diet, there may have been a sudden surge in prostaglandins, thromboxanes, and leukotrienes, and excitability of neural and muscle cells, resulting in severe muscular tightening. Other mechanisms related to the lipids may be involved that are not yet understood.

Fatty acids' relationship with musculoskeletal disorders is very intricate. There are many studies demonstrating that arachidonic acid and other polyunsaturated fatty acids modulate the function of voltage gated calcium, sodium, and potassium channels, primarily in neural and muscle cells impacting the excitability of the cells. Boland L M, Drzewiecki M M. Polyunsaturated Fatty Acid modulation of voltage-gated ion channels. Cell Biochem Biophys. 2008; 52(2):59-84. Epub 2008 Oct. 2. In some studies changes in muscle fiber type have been observed with changes in amount and type of fatty acids. de Wilde J Mohren R, van den Berg S Boekschoten M, Dijk K W, de Groot P, Miller M, Mariman E. Smit E. Short-term high fat-feeding results in morphological and metabolic adaptations in the skeletal muscle of C57BL/6J mice. Physiol Genomics. 2008 Feb. 19; 32(3):360-9. Epub 2007 Nov. 27. On the skeletal side, bone mass is governed by balanced action of osteoblasts (bone forming cells) and osteoclast (bone resorbing cells). There is increasing evidence that various long-chain polyunsaturated fatty acids and their metabolites affect calcium balance, osteoblastogenesis, osteoclastogenesis, and osteoblast and osteoclast function. Poulsen R C, Moughan P J, Kruger M C. Long-chain polyunsaturated fatty acids and the regulation of bone metabolism. Exp Biol Med (Maywood). 2007 November; 232(10):1275-88. Rahman M M, Bhattacharya A, Fernandes G. Docosahexaenoic acid is more potent inhibitor of osteoclast differentiation in RAW 264.7 cells than eicosapentaenoic acid. J Cell Physiol. 2008 January; 214(1):201-9.

Example 16

A Case Study on Thyroid Disturbances

In a host subject, symptoms of thyroid disturbance with a decrease in omega-3 fatty acids, fatigue and weakness, cold intolerance, hair loss, cold hands and feet, weight gain, insomnia, constipation, depression, poor memory, forgetfulness, and nervousness were observed, which were self-adjusting within optimal fatty acids ranges.

Example 17

A Case Study on Weight Gain, Obesity

In a vegetarian host subject it was discovered that there was a band of optimal quantity and ratio of omega-6 and omega-3 fatty acids, beyond which the subject gained weight. At omega-6 of 11 grams and omega-3 of 2 grams, the subject was at 134 lbs. Upon gradual reduction of omega-3 to 1.2 grams, the subject initially gained 6 lbs., and then after 6 weeks, lost 12 lbs. for an ending weight of 128 lbs. Obesity often has been linked to slow metabolism. In turn, metabolic rate has been linked to cell-membrane composition. Hulbert A J. Membrane fatty acids as pacemakers of animal metabolism. Lipids. 2007 September; 42(9):811-9. Epub 2007 Apr. 27. High polyunsaturated membrane composition may be linked with fast membrane associated processes. Membrane composition influences all aspects of the energy balance equation: electrolyte gradient balance, neuropeptide regulation, gene regulation and glucose regulation.

Example 18

A Case Study on Diabetes

Varying quantities and ratios of omega-6 and omega-3 fatty acids were administered to otherwise healthy subjects to see if very early symptoms of diabetes could be induced. 1-High blood sugar, excessive urine production, excessive thirst and increased fluid intake, blurred vision, unexplained weight gain and lethargy were induced by certain ratios and amounts of omega-6 and omega-3 fatty acids within the context of disclosed compositions. These simulated symptoms with very high levels of omega-3 may also be reversed by reducing the dosage. In one instance, insulin resistance may be associated with low levels of omega-6 fatty acids. Summers L K, Fielding B A, Bradshaw H A, Ilic V, Beysen C, Clark M L, Moore N R, Frayn KN. Substituting dietary saturated fat with polyunsaturated fat changes abdominal fat distribution and improves insulin sensitivity. Diabetologia. 2002 March; 45(3):369-77.

Example 19

A Case Study on Digestive System Disorders

In the host subject, incidences of acid reflux disease, irritable bowels, indigestion, and dyspepsia were observed. Each time omega-6 fatty acids were increased or omega-3 fatty acids were decreased the following symptoms appeared: stomach pain, bloating, heartburn, nausea (upset stomach), and burping; but they all disappeared as the body adjusted to increased omega-6. Omega-6 were tested up to 11 grams. It is hypothesized that beyond that point in the particular host the symptoms would persist. Increasing omega-3 beyond 2 grams caused tight dark pellet-like stools. In the optimal omega-6 and omega-3 balance, bile production was optimal as determined by the yellowish brown color of the stools. It was also observed that mucus production in the alimentary canal was optimal with the proper omega-6 and omega-3 quantities and ratio, using mucus production in the oral cavity as an indicator. Halitosis was also observed with 2 grams of omega-3, and got worse when omega-3 were reduced, and then normalized over a period of 3-6 weeks. Arachidonic acid plays a pivotal role in protection and integrity of the intestinal mucosa. Excessive omega-3 can displace arachidonic acid leading to gastrointestinal mucosal damage.

Example 20

A Case Study on Ovulation, Reproductive Disorders

In a host subject, a 35-year old female, cessation of ovulation (as indicated by watery pale menstrual cycles), intense ovulation-related pains and anovulatry menstruation at extremely low omega-6 fatty acids in diet were observed; olive oil being the main fat source. It is hypothesized herein that this was due to deficiency of omega-6 derived prostaglandins, which aid ovulation. The same phenomenon was observed when the subject was put on Advil, which blocks cyclooxygenase activity and therefore the prostaglandin synthesis.

Dietary fatty acids are intricately linked with reproduction from menstruation, to fertilization, to gestation-related complications such as diabetes, to development of the fetus, to pre-term delivery, to post-natal health of the mother and the child.

Example 21

Case Studies on Aging, Tissue Repair

In host subjects, symptoms of aging were modulated by balancing and optimizing omega-6 and omega-3 fatty acids via the disclosed compositions, including muscle mass restoration, stabilizing sleep, increasing mental sharpness, increasing energy and vigor, improved skin, reduction in hair loss, improving bowel function, improving libido and sexual function, and weight management. The management of frequent urination with the ideal balance of omega-6 and omega-3 through the disclosed compositions was also observed. It is hypothesized that this is due to combined effect of management of omega-6 and omega-3 fatty acids in tissue, related eicosanoids, and their effect on physiological functions, and due to the sex-hormone-like effect of these lipids, and due to their effect on the optimization of sex hormone production; further aided by antioxidants and phytochemicals in the compositions.

It has been suggested that lipid per-oxidation, though required at moderate levels, amy be a significant factor in aging. Oxidative stress may also damage other important biological molecules such as nucleic acids and proteins. Hulbert, AJ. "Life and Death: Metabolic Rate, Membrane Composition, and Life Span of Animals" Physiol Rev. 2007 October;87 (4):1175-213. Although membrane fluidity may be associated with youth, introducing of more and more double bonds beyond the first 2-3 may not yield additional fluidity. The disclosed compositions make effective use of natural antioxidants and phytochemcials to manage per-oxidation and retain membrane fluidity, while avoiding excessive omega-3 deliver; omega-3 family of fatty acids with 3-6 double bonds, are the fatty acids most susceptible to per-oxidation. The fibroblast is a type of cell that synthesizes the extra-cellular matrix and collagen, the structural framework for animal tissues. Proper fibroblast function is essential for optimal tissue repair and regeneration. Polyunsaturated fatty acids, antioxidants, and sterols may create a favorable fibroblast plasma membrane environment, and are believed to play a role in electrochemical gradient across the bilayer-lipid membrane. Schroeder F, Kier A B, Sweet W D. Role of polyunsaturated fatty acids and lipid peroxidation in LM fibroblast plasma membrane transbilayer structure. Arch Biochem Biophys. 1990 January; 276(1):55-64. Haines T H. Do sterols reduce proton and sodium leaks through lipid bilayers? Prog Lipid Res. 2001 July; 40(4):299-324. The present disclosure also provides compositions and methods for tissue repair and/or regeneration by induction and maintenance of endogenous stem cell proliferation and/or differentiate. Intestinal cells and bone marrow cells offer examples of adult stem cells for their abundance and their role in the continuous, lifelong, physiological replenishment of circulating cells. The disclosed compositions and methods also restrict calories, which may extend life by restricting oxidative stress and yielding lower membrane unsaturation index.

Example 22

A Case Study on Pulmonary Disorders

In a host subject, an increase of omega-6 fatty acids or a decrease of omega-3 fatty acids was associated with breathing difficulty, nasal congestion, earache, sneezing, and excess mucus. But within the optimal ranges of omega-6 and omega-3, it was self-adjusting over a period of time. A low-fat diet, primarily monounsaturated fats, a total essential fatty acid (EFA) supplement of 1 gram, and a fish oil supplement caused dyspnea in the host subject. The dyspnea disappeared when supplemented with 10-11 grams of omega-6. It is hypothesized that the EFA supplement was not adequately producing the required leukotrienes. Omega-6 and omega-3-derived leukotrienes are very important agents in lung function. They help bring the needed cells to the tissue, and they increase vascular permeability. In excess they can cause airflow obstruction, increased secretion and accumulation of mucus, bronchial constriction, and inflammation. The adjustment period indicates that sudden and wide changes in EFA may upset the immune system, creating a period of heightened vulnerability to pathogens. Further studies may find a link with susceptibility to common colds and influenza with sudden and wide changes in omega-6 and omega-3 fatty acids.

Example 23

A Case Study on Ophthalmologic Disorders

In a host subject, dry eye and pressure-like ache in the eye was observed upon reduction of omega-3 and an increase of omega-6 fatty acids. When levels of omega-6 and omega-3 were kept within suitable ranges by demographic type, the symptoms disappeared over time. It was also observed that drusen, excessive eye mucus that often gathers in the corners of the eyes, could be gotten rid of with proper omega-6 and omega-3 balance in the context of the compositions of the present disclosure. However, when omega-6 or omega-3 were excessively increased the dry eye syndrome persisted. Excessive omega-3 also resulted in very thin blood, possibly due to thromboxanes action reduction, and therefore caused blood-shot eyes.

Docosahexaenoic acid (omega-3) is an important component of retinal photoreceptors and brain synaptic membranes, and arachidonic acid (omega-6) is an important component of vascular endothelial cells. Moreover, since omega-6 also has a role in vascular blood pressure, both omega-6 and omega-3 are critical to optic health. Although omega-3 fatty acids, and formulations of vitamins C, E, beta-carotene, and zinc have been shown to be preventative in progression of age-related macular degeneration (AMD); increased intakes of lutein/xeaxanthin and omega-3 fatty acids are associated with progression of AMD, whereas lower intakes lutein/xeaxanthin and omega-3 are associated with greater optic health; suggesting the role of phytochemicals, and the importance of dosage. Robman L, Vu H, Hodge A, Tikellis G, Dimitrov P, McCarty C, Guymner R. Dietary lutein, zeaxanthin, and fats and the progression of age-related macular degeneration. Can J. Ophthalmol. 2007 October; 42(5):720-6.

Example 24

Case Studies on Dermatological Disorders

Host subjects demonstrated large amounts of omega-3 fatty acids in the diet increased the size of the skin pores, whereas large amounts of omega-6 fatty acids in the diet made skin dry. Balancing the two gave the best results. Fine lines may be reduced using the correct balance in the context of the disclosed compositions. Omega-3 reductions, at times, may be associated with the appearance of a rash around the neck area. It is hypothesized that a sudden increase in cytokine activity from an increase in omega-6 metabolism produced the skin rash. Brittle nails and foot corns and calluses may disappear with the proper balance of fatty acids through the disclosed compositions. Sloughing of skin, as in dead cells coming to the surface after omega-3 fatty acids reduction, was also observed.

Skin displays highly active metabolism of polyunsaturated fatty acids. Deficiency of dietary omega-6, linoleic acid has been shown to result in scaly dermatoses and disruption of the skin barrier system. Linoleic acid intake combined with high intakes of vitamin C are associated with better skin-aging appearance. Dietary hempseed oil has been shown to cause significant changes in plasma fatty acid profiles and improved clinical symptoms of atopic dermatitis, which may be due to the abundant supply of both omega-6 and omega-3 fats in hempseed oil. Ziboh V A. Prostaglandins, leukotrienes, and hydroxy fatty acids in epidermis. Semin Dermatol. 1992 Jun.; 11(2):114-20. Ziboh V A, Cho Y, Mani I, Xi S. Biological significance of essential fatty acids/prostanoids/lipoxygenase-derived monohydroxy fatty acids in the skin. Arch Pharm Res. 2002 Dec.; 25(6):747-58. Cosgrove M C, Franco O H, Granger S P, Murray P G, Mayes A E. Dietary nutrient intakes and skin-aging appearance among middle-aged American women. Am J Clin Nutr. 2008 August; 88(2):480.

Example 25

Case Studies on Sleep Disorders

It was observed that use of optimized levels of omega-6 and omega-3 fatty acids through the disclosed lipid compositions by demographic type, more restful sleep and normalization of sleep and wake hours in host subjects may be achieved. In fact, a more restful sleep with a sleep time reduction to 7 hours from 8 in one host subject, over time was observed. Restless leg syndrome may also be relieved in host subjects. Each time omega-6 and omega-3 amounts were changed the host went through an adjustment period. Omega-3 was more sleep inducing, and increased the total sleep time; omega-6 though was sleep-inducing at first caused a strong rebound of awakening a few hours later, to the point of causing temporary insomnia, but over two weeks sleep patterns normalized. It is hypothesized this is because of the effect of omega-6 and omega-3 fatty acids on thyroid function and the effect of thyroid function on sleep, among other mechanisms, such as PGD2 action.

Omega-6 metabolite PGD2 is believed to be a strong sleep-inducing agent, with a strong rebound of wakefulness reaching insomnia, and a dose-dependent bell-shaped response curve. In other studies omega-3-deficient diet has been shown to lessen the pineal melatonin rhythm, weaken the endogenous functioning of the circadian clock, and to play a role in nocturnal sleep disturbances. Among other fatty acids, palmitoleic and oleic acid have been shown to be important for sleep disorders, perhaps due to their function as precursors of the sleep inducing oleamide.

Example 26

A Case Study on Dental Diseases

In a vegetarian host subject, less dental sensitivity, reversal of gum receding, brightening of tooth enamel, and lessening of dental spots and plaque were observed when omega-3 fatty acids were reduced from 2 grams to 1.2 grams while holding omega-6 constant at 11 grams. Lipid compositions comprising nuts and oils were the source of omega-6 and omega-3 fatty acids. There was an adjustment period of 3-6 weeks, when the symptoms got worse in the host subjects before getting better. Longer-term intervention studies should be able to test the hypothesis by studying tooth loss during the intervention period. Bioactivity of lipids may explain the linkage between periodontitis/tooth loss and coronary heart disease.

Example 27

Case Studies on Immunity, Autoimmune and Infectious and Inflammatory Diseases

In a vegetarian host subject, a 48-year old menopausal woman, on 11 g of LA and 1.8 g of ALA, from oils and nuts, spinal burning sensation, heat in the body, skin and feet, and delayed wound healing were observed. The subject also developed vaginal yeast infection. Symptoms disappeared upon reducing ALA to 1.2 g after an initial adjustment period. It is hypothesized that omega-6 and omega-3 fatty acid imbalance leads to inflammation, compromised immunity, and infection, particularly during the adjustment period following large changes in dietary fatty acids. It is further suspected that both omega-6 and omega-3 are anti-inflammatory in small doses and inflammatory in large doses, particularly in light of possible interactions with phytochemicals. In one embodiment, excessive suppression of the immune system through omega-3, phytochemical, and other dietary constituents may lead to up-regulation of compensatory mechanisms causing dysregulated inflammation leading to a numebr of diseases. Therefore, it is an embodiment of the disclosure that net effect of all dietary immunomodulation below the threshold where self-regulation of the immune system is suppressed may be more effective nutritional approach.

It is understood that the total percent by weight of any combination of components does not exceed 100%. It is also understood that if a component is present in a composition, then the component is present in a non-zero amount (for example, more than about 0.00000001 mg or percent by weight of total weight).

The amounts and ratios of various nuts, seeds, lipids, and oil, to name a few, of the present embodiments were discovered to be beneficial, including by links to benefits for various diseases and conditions, as set forth above, empirically by outcome focused experimentation. The above recited examples, case studies, links with particular medical conditions, and the like are not meant to limit the present disclosure, but merely to explain the disclosure by way of example.

While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of preparing a lipid-containing formulation for a subject, comprising:
   combining daily amounts of fatty acids for the subject based on one or more factors selected from: age of the subject, gender of the subject, diet of the subject, the body weight of the subject, physical activity level of the subject, lipid tolerance of the subject, medical conditions of the subject, family medical history of the subject, and ambient temperature range of the subject's living area,
   wherein the formulation comprises omega-6 and omega-3 fatty acids, and wherein the ratio of omega-6 to omega-3 fatty acids and/or their amounts are controlled based on the one or more factors; wherein, the formulation provides a dosage of omega-6 and omega-3 at an omega-6 to omega-3 ratio of:
      4:1 or greater, wherein dosage of omega-6 fatty acids is not more than 40 grams; or
      1:1 to 10:1 if the subject has a diet of low antioxidants and/or low phytochemicals; or
      4:1 to 45:1 if the subject has a diet of high antioxidants and/or high phytochemicals; or
      2:1 to 30:1 if the subject has a diet of high seafood; or
      1:1 to 45:1 based on lipid tolerance of the subject; or
      1:1 to 50:1 if the subject has a condition wherein gradual increase of omega-6 and/or
   gradual withdrawal of omega-3 is necessary; or
   wherein, the fatty acid content is matched to Table 6;
   wherein the formulation produced by the method is not a specific variety of a fruit, a vegetable, a grain, a legume, a nut, or a seed.

2. The method of claim 1, wherein
   (i) the ratio of omega-6 to omega-3 fatty acid is in the range of 4:1 to 45:1;
   (ii) the ratio of omega-6 to omega-3 fatty acids is greater than 6:1; or
   (iii) the ratio of omega-6 to omega-3 fatty acid is at least 9:1.

3. The method of claim 1, wherein the formulation further comprises omega-9 fatty acids, where the omega-9 fatty acids are in the range of 10% to 90% by weight of total lipids.

4. The method of claim 1, wherein omega-6 fatty acids are in the range of 4% to 75% by weight of total lipids.

5. The method of claim 1, wherein the formulation further comprises monounsaturated fatty acids and saturated fatty acids, wherein the ratio of total fatty acids to monounsaturated fatty acids is in the range of 1:1 to 15:1; and/or the ratio of total fatty acids to saturated fatty acids is 1:1 to 15:1.

6. The method of claim 1, wherein the formulation further comprises one or more fatty acids selected from butyric acid (C4:0), lauric acid (C12:0), myristic acid (C14:0), palmitic acid (C16:0), stearic acid (C18:0), arachidic acid (C20:0), myristoleic acid (C14:1), palmitoleic acid (C16:1), oleic acid (C18:1), gadoleic acid (C20:1), ercucic acid (C22:1), nervonic acid (C24:1), linoleic acid (C18:2), conjugated-linoleic acid (C18:2), gamma-linolenic acid (C18:3), eicosadienoic acid (C20:2), di-homo-gamma-linolenic acid (C20:

3), arachidonic acid (C20:4), alpha-linolenic acid (C18:3), stearidonic acid (C18:4), eicosapentaenoic acid (C20:5), docosapentaenoic acid (C22:5), and docosahexaenoic acid (C22:6).

7. The method of claim 1, wherein the formulation comprises one or more nutrients effective to reduce omega-3 requirement and/or allow for higher omega-6:omega-3 ratio than in the absence of the nutrient, and/or increase effective levels of omega-3 in a subject.

8. The method of claim 1, wherein the formulation comprises one or more polyphenols, and is effective to increase omega-3 levels in the subject.

9. The method of claim 1, wherein the formulation comprises one or more polyphenols selected from: a flavonoid, a flavonol, a flavanone, a flavone, an isoflavone, an anthocyanidin, an anthocyanin, a phytoestrogen, a catechin, a quercetin, a kaempferol, resveratrol, a lignan, phenolic acids, gallic acid, ellagic acid, hydroxycinnamic acid, and curcumin.

10. The method of claim 1, wherein the formulation further comprises one or more of phytochemicals, antioxidants, vitamins, and minerals, including vitamin A, folic acid or folate, vitamin, C, vitamin D, vitamin E, Cu, Zn, Mn, Fe, Se, and/or Mg.

11. The method of claim 1, wherein the formulation comprises one or more of oils, butters, nuts or their oils, seeds or their oils, legumes, dairy, cocoa, lentils, and grains.

12. The method of claim 1, wherein the formulation comprises fatty acids, phytochemical, antioxidant, vitamins and minerals in amounts designed for the subject to maintain oxidant balance, antioxidant balance, inflammation balance, and/or avoid unfavorable dietary interactions.

13. The method of claim 1, wherein the formulation is in the form of enteral, parenteral, a liquid, semi-solid, solid, granule, drop, gel, powder, capsule, tablet, lozenge, pill or a combination thereof.

14. The method of claim 1, wherein the formulation is in the form of a meal or dietary component selected from an oil, sauce, spread, dressing, butter, drops, salad, side dish, bar, bread, dessert, pastry, truffle, pudding, cake, bakery product, yogurt, drink, dairy product, or a combination thereof.

15. The method of claim 1, wherein the factors are as set forth in Tables 7, 8, 9, 10, 11, 12, 13, 14, 15, 16, 17, 18, 19, or 20, or wherein three or more components are selected from Table 6.

16. The method of claim 1, the formulation further comprising one or more phytochemicals selected from: phytosterol, campesterol, sitosterol, stigmasterol, organosulfur, sulfide, melatonin, carotenoid, beta carotene, lycopene, lutein, zeaxanthin, a phenol.

17. The method of claim 1, wherein the formulation is administered in one-part or comprises multi-part mutually complementing components, for one or more days, one or more weeks, or one or more months.

18. The method of claim 1, whereby the formulation provides a substitution and/or supplementation of lipids that are typically added to food preparations so that when the formulation is provided in combination with a no-lipid or low-lipid food product, the combination of the formulation and the food preparation provides a balanced lipid intake to a subject ingesting the combination.

19. The method of claim 1, wherein lipid-free or low-lipid foods are prepared for and/or provided in combination with said lipid formulation.

20. The method of claim 19, wherein foods are selected from one or more of grains, legumes, fruits, vegetables, herbs or spices, sweeteners, yogurt, beverages, eggs, cheese, milk, poultry, seafood, and meat.

21. The method of claim 1, wherein the method comprises determining for the subject a diet type based on one or more of amount and type of antioxidants, phytochemicals, vitamins, minerals, seafood, legumes, fruits, vegetables, whole grains, herbs, spices, and sweeteners in the diet and/or whether or not the diet is omnivorous, vegetarian, vegan, or ovo-lacto vegetarian.

22. The method of claim 1, wherein omega-3 fatty acids are in the range of 0.1% to 30% by weight of total lipids.

23. The method of claim 1, wherein the formulation further comprises monounsaturated fatty acids, and wherein the ratio of monounsaturated fatty acids to polyunsaturated fatty acids is in the range of 0.25:1 to 6:1.

24. The method of claim 1, wherein the formulation comprises fat, and wherein the dosage of total fat in grams is from 10-100 grams, or is 10-75 grams, or is 15-80 grams, or is 20-100 grams.

25. The method of claim 1, wherein the dosage of omega-6 fatty acids is less than 40 grams, or from 1 to 10 grams, or from 2 to 15 grams, or from 2 to 25 grams, or from 1 to 40 grams, or from 2 to 40 grams.

26. The method of claim 1, wherein the dosage of omega-3 fatty acids is from 0.1 to 1.0 grams, or from 0.2 to 1.0 grams, or from 1.0 to 2.0 grams, or from 2.0 to 3.0 grams, or from 2.0 to 4.0 grams, or from 2.0 to 6.0 grams.

27. The method of claim 1, wherein the formulation comprises monounsaturated fatty acids and fat, and wherein the dosage of total fat is 10-100 grams, the dosage of omega-6 fatty acids is from 1 to 40 grams; the dosage of omega-3 fatty acids is from 0.1 to 5 grams, the ratio of monounsaturated fatty acids to polyunsaturated fatty acids is in the range of 1:1 to 3:1, the ratio of monounsaturated fatty acids to saturated fatty acids is 1:1 to 5:1, the ratio of omega-9 to omega-6 fatty acids is in the range of 1:1-3:1, and the ratio of omega-6 to omega-3 fatty acids is in the range of 4:1 to 45:1.

28. The method of claim 1, wherein the formulation supplies 60-90% of the diet's fat calories.

29. The method of claim 1, wherein 20-45% of a diet's calories are from fat, 45-65% of a diet's calories are from carbohydrates, and 10%-25% of a diet's calories are from protein.

30. The method of claim 1, wherein the formulation comprises one or more of the following:
  (i) dosage of eicosapentaenoic acid (C20:5) not more than 0.5 grams, and/or a dosage of docosahexaenoic acid (C22:6) not more than 0.2 grams;
  (ii) dosage of phytosterols less than 150 mg;
  (iii) one or more of: dosage of campesterol less than 1.5 mg, dosage of sitosterol less than 30 mg, and dosage of stigmasterol less than 1.5 mg;
  (iv) one or more of: dosage of vitamin A less than 30000 IU, dosage of folic acid or folate less than 800 mcg, dosage of vitamin C less than 400 mg, dosage of vitamin D less than 400 IU, dosage of vitamin E tocopherol beta less than 0.5 mg, dosage of vitamin E tocopherol delta less than 0.5 mg, dosage of vitamin E tocopherol gamma less than 4 mg, dosage of vitamin E tocopherol alpha less than 15 mg, dosage of copper less than 3 mg, dosage of zinc less than 14 mg, dosage of manganese less than 8 mg, dosage of iron less than 18 mg, dosage of selenium less than 80 mcg, and dosage of magnesium less than 700 mg;
  (v) one or more of: dosage of alpha carotene less than 4000 mcg, dosage of beta carotene less than 14000 mcg, dosage of beta cryptoxanthin less than 850 mcg, dosage of betaine less than 50 mg, dosage of choline less than 250 mg, dosage of lycopene less than 1900 mcg, and dosage of lutein/zeaxanthin less than 14000 mcg;
(vi) vitamin E in the range of 0.001% to 0.5% by weight of total lipids; or
(vii) dosage of fiber less than 45 g.

31. The method of claim 1, wherein the formulation comprises omega-9 fatty acids, wherein the ratio of omega-9 fatty acids to omega-6 fatty acids is from 1:1 to 3:1.

32. A method of selecting a lipid-containing formulation for administering to a subject, comprising:
a) evaluating the subject on the basis of one or more factors selected from: age of the subject, gender of the subject, diet of the subject, the body weight of the subject, physical activity level of the subject, lipid tolerance of the subject, medical conditions of the subject, family medical history of the subject, and ambient temperature range of the subject's living area, and
b) combining daily amounts of fatty acids comprising omega-6 and omega-3 fatty acids, wherein the ratio of omega-6 to omega-3 fatty acids and/or their amounts are controlled based on the one or more factors; wherein, the formulation provides a dosage of omega-6 and omega-3 at an omega-6 to omega-3 ratio of
4:1 or greater, wherein dosage of omega-6 fatty acids is not more than 40 grams; or
1:1 to 10:1 if the subject has a diet of low antioxidants and/or low phytochemicals; or
4:1 to 45:1 if the subject has a diet of high antioxidants and/or high phytochemicals; or
2:1 to 30:1 if the subject has a diet of high seafood; or
1:1 to 45:1 based on lipid tolerance of the subject; or
1:1 to 50:1 if the subject has a condition wherein gradual increase of omega-6 and/or
gradual withdrawal of omega-3 is necessary; or
wherein, the fatty acid content is matched to Table 6;
wherein the formulation produced by the method is not a specific variety of a fruit, a vegetable, a grain, a legume, a nut, or a seed.

33. The method of claim 32, wherein the method comprises determining for the subject a diet type based on one or more of amount and type of antioxidants, phytochemicals, vitamins, minerals, seafood, legumes, fruits, vegetables, whole grains, herbs, spices, and sweeteners in the diet, and/or whether or not the diet is omnivorous, vegetarian, vegan, or ovo-lacto vegetarian.

34. The method of claim 32, wherein phytochemicals and nuts and seeds are minimized or eliminated to avoid unfavorable interactions.

35. The method of claim 32, wherein the formulation comprises one or more of oils, butters, nuts or their oils, seeds or their oils, legumes, dairy, cocoa, lentils, and grains.

36. The method of claim 32, wherein lipid-free or low-lipid foods are designed for and/or provided in combination with said lipid formulation.

37. The method of claim 32, whereby the lipid-containing formulation provides a substitution and/or supplementation of lipids that are typically added to food preparations so that when the formulation is provided in combination with a no-lipid or low-lipid food product, the combination of the formulation and the food preparation provides a balanced lipid intake to a subject ingesting the combination.

38. The method of claim 36, the formulation comprising foods selected from one or more of grains, legumes, fruits, vegetables, yogurt, herbs or spices, sweeteners, beverages, eggs, cheese, milk, poultry, seafood, and meat.

39. The method of claim 32, wherein the formulation is in the form of enteral, parenteral, a liquid, semi-solid, solid, granule, drop, gel, powder, capsule, tablet, lozenge, pill, or a combination thereof.

40. The method of claim 32, wherein the formulation is in the form of a meal or dietary component selected from an oil, sauce, spread, dressing, butter, drops, salad, side dish, bar, bread, dessert, pastry, truffle, pudding, cake, bakery product, dairy product, yogurt, drink, or a combination thereof.

41. The method of claim 32, wherein the formulation is administered in one-part or comprises multi-part mutually complementing components, for one or more days, one or more weeks, or one or more months.

42. The method of claim 32, wherein the formulation comprises one or more fatty acids selected from butyric acid (C4:0), lauric acid (C12:0), myristic acid (C14:0), palmitic acid (C16:0), stearic acid (C18:0), arachidic acid (C20:0), myristoleic acid (C14:1), palmitoleic acid (C16:1), oleic acid (C18:1), gadoleic acid (C20:1), ercucic acid (C22:1), nervonic acid (C24:1, linoleic acid (C18:2), conjugated-linoleic acid (C18:2), gamma-linolenic acid (C18:3), eicosa-dienoic acid (C20:2), di-homo-gamma-linolenic acid (C20:3), arachidonic acid (C20:4), alpha-linolenic acid (C18:3), stearidonic acid (C18:4), eicosapentaenoic acid (C20:5), docosapentaenoic acid (C22:5), and docosahexaenoic acid (C22:6).

43. The method of claim 32, wherein omega-6 fatty acids are present at 4% to 75% by weight of total lipids.

44. The method of claim 32, wherein omega-3 fatty acids are 0.1% to 30% by weight of total lipids.

45. The method of claim 32, wherein the formulation comprises omega-9 fatty acids, and wherein omega-9 fatty acids are present at 10% to 90% by weight of total lipids.

46. The method of claim 32, wherein
(i) the ratio of omega-6 to omega-3 fatty acid is in the range of 4:1 to 45:1;
(ii) the ratio of omega-6 to omega-3 fatty acids is greater than 6:1; or
(iii) the ratio of omega-6 to omega-3 fatty acid is at least 9:1.

47. The method of claim 32, wherein the formulation comprises monounsaturated fatty acids, and wherein the ratio of monounsaturated fatty acids to polyunsaturated fatty acids is in the range of 0.25:1 to 6:1.

48. The method of claim 32, wherein the formulation comprises saturated fatty acids and monounsaturated fatty acids, and wherein the ratio of total fatty acids to monounsaturated fatty acids is in the range of 1:1 to 15:1; and/or the ratio of total fatty acids to saturated fatty acids is 1:1 to 15:1.

49. The method of claim 32, wherein the formulation comprises fat, and wherein the dosage of total fat in grams is from 10-100 grams, or is 10-75 grams, or is 15-80 grams, or is 20-100 grams.

50. The method of claim 32, wherein the dosage of omega-6 fatty acids is less than 40 grams, or from 1 to 10 grams, or from 2 to 15 grams, or from 2 to 25 grams, or from 2 to 40 grams.

51. The method of claim 32, wherein the dosage of omega-3 fatty acids is from 0.1 to 1.0 grams, or from 0.2 to 1.0 grams, or from 1.0 to 2.0, or from 2.0 to 3.0 grams, or from 2.0 to 4.0 grams, or from 2.0 to 6.0 grams.

52. The method of claim 32, wherein the formulation comprises monounsaturated fatty acids, saturated fatty acids, and fat, and wherein the dosage of total fat is 10-100 grams, the dosage of omega-6 fatty acids is from 1 to 40 grams; the dosage of omega-3 fatty acids is from 0.1 to 5 grams, the ratio of monounsaturated fatty acids to polyunsaturated fatty acids is in the range of 1:1 to 3:1, the ratio of monounsaturated fatty acids to saturated fatty acids is 1:1 to 5:1, the ratio of omega-9 to omega-6 fatty acids is in the range of 1:1-3:1, and the ratio of omega-6 to omega-3 fatty acids is in the range of 4:1 to 45:1.

53. The method of claim 32, wherein the formulation comprises one or more polyphenols selected from: a flavonoid, a flavonol, a flavanone, a flavone, an isoflavone, an anthocyanidin, an anthocyanin, a phytoestrogen, a catechin, a quercetin, a kaempferol, resveratrol, a lignan, phenolic acids, gallic acid, ellagic acid, hydroxycinnamic acid, and curcumin.

54. The method of claim 32, the formulation comprising one or more phytochemicals selected from: phytosterol, campesterol, sitosterol, stigmasterol, organosulfur, sulfide, melatonin, carotenoid, beta carotene, lycopene, lutein, zeaxanthin, a phenol.

55. The method of claim 32, the formulation comprising one or more phytochemicals, antioxidants, vitamins, minerals, and trace elements, including vitamin A, folic acid or folate, vitamin, C, vitamin D, vitamin E, Cu, Zn, Mn, Fe, Se, and/or Mg.

56. The method of claim 32, wherein the formulation comprises fatty acids, phytochemical, antioxidant, vitamins and minerals in amounts designed for the subject to maintain oxidant balance, antioxidant balance, inflammation balance, and/or avoid unfavorable dietary interactions.

57. The method of claim 32, wherein the factors are as set forth in Tables 7, 8, 9, 10, 11, 12, 13, 14, 15, 16, 17, 18, 19, or 20, or wherein three or more components are selected from Table 6.

58. The method of claim 32, wherein the formulation supplies 60-90% of the diet's fat calories.

59. The method of claim 32, wherein 20-45% of a diet's calories are from fat, 45-65% of a diet's calories are from carbohydrates, and 10%-25% of a diet's calories are from protein.

60. The method of claim 32, wherein the formulation is configured for gradual and/or steady administration, wherein any omega-3 withdrawal is gradual, and/or any omega-6 and/or other fatty acid increase is gradual.

61. The method of claim 32, wherein the one or more nutrients alleviate one or more symptoms associated with a disease or condition selected from menopause, aging, musculoskeletal disorders, mood swing, reduced cognitive function, neural disorders, mental disorders, thyroid disturbances, weight gain, obesity, diabetes, endocrine disorders, digestive system disorders, reproductive disorders, pulmonary disorders, renal diseases, ophthalmologic disorders, dermatological disorders, sleep disorders, dental diseases, cancer, autoimmune diseases, infectious diseases, inflammatory diseases, hypercholesterolemia, dyslipidemia or cardiovascular disease.

62. The method of claim 32, wherein the formulation comprises one or more of the following:
(i) dosage of eicosapentaenoic acid (C20:5) not more than 0.5 grams, and/or a dosage of docosahexaenoic acid (C22:6) not more than 0.2 grams;
(ii) dosage of phytosterols less than 150 mg;
(iii) one or more of: dosage of campesterol less than 1.5 mg, dosage of sitosterol less than 30 mg, and dosage of stigmasterol less than 1.5 mg;
(iv) one or more of: dosage of vitamin A less than 30000 IU, dosage of folic acid or folate less than 800 mcg, dosage of vitamin C less than 400 mg, dosage of vitamin D less than 400 IU, dosage of vitamin E tocopherol beta less than 0.5 mg, dosage of vitamin E tocopherol delta less than 0.5 mg, dosage of vitamin E tocopherol gamma less than 4 mg, dosage of vitamin E tocopherol alpha less than 15 mg, dosage of copper less than 3 mg, dosage of zinc less than 14 mg, dosage of manganese less than 8 mg, dosage of iron less than 18 mg, dosage of selenium less than 80 mcg, and dosage of magnesium less than 700 mg;
(v) one or more of: dosage of alpha carotene less than 4000 mcg, dosage of beta carotene less than 14000 mcg, dosage of beta cryptoxanthin less than 850 mcg, dosage of betaine less than 50 mg, dosage of choline less than 250 mg, dosage of lycopene less than 1900 mcg, and dosage of lutein/zeaxanthin less than 14000 mcg;
(vi) vitamin E in the range of 0.001 % to 0.5 % by weight of total lipids; or
(vii) dosage of fiber less than 45 g.

63. The method of claim 32, wherein the formulation comprises omega-9 fatty acids, wherein the ratio of omega-9 fatty acids to omega-6 fatty acids is from 1:1 to 5:1.

64. A method of ameliorating one or more symptoms of a medical condition in a subject, comprising
(a) producing a lipid-containing formulation by the method of claim 1; and
(b) administering said lipid-containing formulation to the subject.

65. The method of claim 64, wherein a disease or condition is selected from menopause, aging, musculoskeletal disorders, mood swing, reduced cognitive function, neural disorders, mental disorders, thyroid disturbances, weight gain, obesity, diabetes, endocrine disorders, digestive system disorders, reproductive disorders, pulmonary disorders, renal diseases, ophthalmologic disorders, dermatological disorders, sleep disorders, dental diseases, cancer, autoimmune diseases, infectious diseases, inflammatory diseases, hypercholesterolemia, dyslipidemia or cardiovascular disease.

66. A method of ameliorating one or more symptoms of a medical condition in a subject, comprising
(a) producing a lipid-containing formulation by the method of claim 32; and
(b) administering said lipid-containing formulation to the subject.

67. The method of claim 66, wherein a disease or condition is selected from menopause, aging, musculoskeletal disorders, mood swing, reduced cognitive function, neural disorders, mental disorders, thyroid disturbances, weight gain, obesity, diabetes, endocrine disorders, digestive system disorders, reproductive disorders, pulmonary disorders, renal diseases, ophthalmologic disorders, dermatological disorders, sleep disorders, dental diseases, cancer, autoimmune diseases, infectious diseases, inflammatory diseases, hypercholesterolemia, dyslipidemia or cardiovascular disease.

* * * * *

UNITED STATES PATENT AND TRADEMARK OFFICE
CERTIFICATE OF CORRECTION

PATENT NO. : 10,292,958 B2
APPLICATION NO. : 13/332251
DATED : May 21, 2019
INVENTOR(S) : Urvashi Bhagat It is certified that error appears in the above-identified patent and that said Letters Patent is hereby corrected as shown below:

In the Specification

At Column 7, Line 66, please replace "Irving" with --living--.

At Column 12, Line 31, please replace "(C 8:4)" with --(C18:4)--.

At Column 15, Lines 16-19 in Table 3 please remove the underlining under "Grains"; indent before "Brown Rice", "Whole Wheat", and "Other"; and insert a blank line between the line beginning with "Other" and the line beginning with "Vegetables.".

At Column 15, Lines 29-33 in Table 3 please remove the underlining under "Lipids"; indent before "C4:0", "C22:6 w/3", and "Other"; and insert a blank line between the line beginning with "Other" and the line beginning with "Carbohydrates.".

At Column 15, Line 63, please replace "body food" with --baby food--.

At Column 17, Line 40, please replace "Table 3" with --Table 4--.

At Column 27, Line 52, please replace "Eggs<2.5%" with --Eggs<25%--.

At Column 33, Line 64, please replace "(%-6%)" with --(1%-6%)-- and "(2%-5%)" with --(2%-15%)--.

At Column 34, Line 67, please replace "(2%-36)" with --(2%-36%)"--.

At Column 35, Line 36, please replace "(4-35)" with --(4%- 35%)--.

At Column 43, Line 23, please delete "1-".

Signed and Sealed this
First Day of October, 2019

Andrei Iancu
*Director of the United States Patent and Trademark Office*

CERTIFICATE OF CORRECTION (continued)
U.S. Pat. No. 10,292,958 B2

In the Claims

At Column 48, Line 37, please replace "Table 6" with --Table 7--.

At Column 51, Line 39, please replace "Table 6" with --Table 7--.

At Column 52, Line 23, please replace "(C24:1" with --(C24:1)--.

UNITED STATES PATENT AND TRADEMARK OFFICE
CERTIFICATE OF CORRECTION

| | |
|---|---|
| PATENT NO. | : 10,292,958 B2 |
| APPLICATION NO. | : 13/332251 |
| DATED | : May 21, 2019 |
| INVENTOR(S) | : Urvashi Bhagat |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 178 days.

Signed and Sealed this
Seventh Day of February, 2023

Katherine Kelly Vidal
*Director of the United States Patent and Trademark Office*